(12) United States Patent
Meng et al.

(10) Patent No.: US 10,072,300 B2
(45) Date of Patent: Sep. 11, 2018

(54) KIT FOR THE PROGNOSIS OF COLORECTAL CANCER

(71) Applicant: BIOMÉRIEUX, Marcy l'Etoile (FR)

(72) Inventors: Xia Meng, Shanghai (CN); Qinghua Xu, Shanghai (CN); Xun Ye, Shanghai (CN); Fang Liu, Shanghai (CN); Fei Wu, Shanghai (CN)

(73) Assignee: BIOMERIEUX, Marcy l'Etoile (FR)

( * ) Notice: Subject to any disclaimer, the term of this patent is extended or adjusted under 35 U.S.C. 154(b) by 221 days.

(21) Appl. No.: 14/893,394

(22) PCT Filed: May 20, 2014

(86) PCT No.: PCT/CN2014/077944
§ 371 (c)(1),
(2) Date: Nov. 23, 2015

(87) PCT Pub. No.: WO2014/187308
PCT Pub. Date: Nov. 27, 2014

(65) Prior Publication Data
US 2016/0177399 A1   Jun. 23, 2016

(30) Foreign Application Priority Data

May 21, 2013 (CN) .......................... 2013 1 0189964

(51) Int. Cl.
C12Q 1/68 (2018.01)
C12Q 1/6886 (2018.01)
G01N 33/574 (2006.01)

(52) U.S. Cl.
CPC ..... *C12Q 1/6886* (2013.01); *G01N 33/57419* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS 7,939,263 B2   5/2011   Clarke et al.

FOREIGN PATENT DOCUMENTS

| CN | 101868729 A | 10/2010 |
|---|---|---|
| CN | 103003444 A | 3/2013 |
| WO | 00/58332 A1 | 10/2000 |
| WO | 2005/005601 A2 | 1/2005 |
| WO | 2011153684 A1 | 12/2011 |
| WO | 2013/001369 A2 | 1/2013 |
| WO | 2013/003625 A2 | 1/2013 |

OTHER PUBLICATIONS

Jan. 3, 2017 Extended European Search Report issued in Patent Application No. 14800653.9.
Han, Mark et al. "Novel Blood-Based, Five-Gene Biomarker Set for the Detection of Colorectal Cancer," Clinical Cancer Research, vol. 14, No. 2, pp. 455-460, 2008.
Marshall, K. W. et al. "A blood-based biomarker panel for stratifying current risk for colorectal cancer," International Journal of Cancer, No. 126, pp. 1177-1186, 2009.
Xu, Qing-hua et al. "Research Progress in Application of Blood-Based Gene Expression Tests for Colorectal Cancer Screening," China Cancer, vol. 22, No. 2, pp. 90-93, 2013.
Oct. 29, 2014 Search Report issued in International Patent Application No. PCT/CN2014/077944.
Han et al., "Novel Blood-Based, Five-Gene Biomarker Set for the Detection of Colorectal Cancer," Clin Cancer Res 2008; 14(2), pp. 455-460, Jan. 15, 2008.
Yi-Chen Dai et al., "Identification of differential gene expressions in colorectal cancer and polyp by cDNA microarray," World Journal of Gastroenterology, vol. 18, Issue 6, pp. 570-575, Feb. 14, 2012.
Hua Ping Gu, et al., "Relationship of expressions of CD15, CD44v6 and nm23H1 mRNA with metastasis and prognosis of colon carcinoma," World Chin J Digestol; 8(8) pp. 887-891, Aug. 8, 2000.
"*Homo sapiens* microsomal glutathione S-transferase 1 (MGST1), transcript variant 1, mRNA," Genbank Accession No. NM_145792.2, accessed at https://www.ncbi.nlm.nih.gov/nuccore/NM_145792.2?report=genbank&to=919, pp. 1-5 (last accessed on May 8, 2018).

*Primary Examiner* — Jehanne S Sitton
(74) *Attorney, Agent, or Firm* — Oliff PLC

(57) ABSTRACT

A kit for the prognosis of colorectal cancer, which includes reagents related in detecting the expression level of any one or more genes of the following five genes: BST1, as shown in SEQ ID NO:1; MGST1, as shown in SEQ ID NO:2, 3, 4, 5, 6, 7, 8, 9 or 10; HP, as shown in SEQ ID NO:11 or 12; RCAN3, as shown in SEQ ID NO:13, 14, 15, 16, 17, 18, 19, 20, 21 or 22; and SRA1, as shown in SEQ ID NO:23 or 24. The reagents are used to detect the expression level of any one or more of the above five genes in the preparation of a kit for the prognosis of colorectal cancer. The kit can be used to perform precise prognosis for a patient suffering from colorectal cancer, and has good clinical application prospects.

28 Claims, 3 Drawing Sheets
Specification includes a Sequence Listing.

```
                        SEQUENCE LISTING

<160> NUMBER OF SEQ ID NOS: 40

<210> SEQ ID NO 1
<211> LENGTH: 1497
<212> TYPE: DNA
<213> ORGANISM: Homo Sapiens

<400> SEQUENCE: 1
aaagtgctgg gattacaggc atgagccgcc gcgccccgcc ccacgctcag tcttgaaatt      60
gtctggaacg ggaaacggca aacagcgaga tatccgagcg agagtcccgc cctgcatcag     120
tttgcggaac cgccttggta gaaggagaga aggggagtgg aggaagcacg ggactggagg     180
gaccaaagtt ccccgatggc ggcccagggg tgcgcggcat cgcggctgct ccagctgctg     240
ctgcagcttc tgcttctact gttgctgctg gcggcgggcg gggcgcgcgc gcggtggcgc     300
ggggagggca ccagcgcaca cttgcgggac atcttcctgg gccgctgcgc cgagtaccgc     360
gcactgctga gtcccgagca gcggaacaag aactgcacag ccatctggga agcctttaaa     420
gtggcgctgg acaaggatcc ctgctccgtg ctgccctcag actatgacct tttattaac      480 ttgtccaggc actctattcc cagagataag tccctgttct gggaaaatag ccacctcctt     540
gttaacagct tgcagacaa caccccgtcgt tttatgcccc tgagcgatgt tctgtatggc     600
agggttgcag atttcttgag ctggtgtcga cagaaaaatg actctggact cgattaccaa     660
tcctgcccta catcagaaga ctgtgaaaat aatcctgtgg attccttttg gaaaagggca     720
tccatccagt attccaagga tagttctggg gtgatccacg tcatgctgaa tggttcagag     780
ccaacaggag cctatcccat caaaggtttt tttgcagatt atgaaattcc aaacctccag     840
aaggaaaaaa ttacacgaat cgagatctgg gttatgcatg aaattggggg acccaatgtg     900
gaatcctgcg gggaaggcag catgaaagtc ctggaaaaga ggctgaagga catggggttc     960
cagtacagct gtattaatga ttaccgacca gtgaagctct tacagtgcgt ggaccacagc    1020
acccatcctg actgtgcctt aaagtcggca gcagccgcta ctcaaagaaa agccccaagt    1080
ctttatacag aacaaaggc gggtcttatc attcccctct ttctggtgct ggcttccagg    1140
actcaactgt aactggaaac tgtgttgctc taaccctcct ccagccctgc agcctcccct    1200
tgcagtcatc attcgtgttc tgtgtatacc aaatgattct gttatctaaa gaagcttttt    1260
gctgggaaaa cgatgtcctg aaaatggtat ttcaatgagg catatgttca ggatttcaga    1320
aacaagaagt tagttctatt tagcaggtta aaaaatgctg cattagaatt aaagcaagtt    1380
attttcttat ttgtataatg acacaaagca ttgggagtca gactgcttgt atattatcaa    1440
acattttaag agaattctaa taaagctgta ttttacatca aaaaaaaaaa aaaaaaa       1497

<210> SEQ ID NO 2
<211> LENGTH: 919
<212> TYPE: DNA
<213> ORGANISM: Homo Sapiens

<400> SEQUENCE: 2
tcgtgacaaa gcaaattgtc tggtatcatg aatttggaac accattccag accaaaattg       60
aaaaaatggt tgacctcacc caggtaatgg atgatgaagt attcatggct tttgcatcct     120
```

```
atgcaacaat tattctttca aaaatgatgc ttatgagtac tgcaactgca ttctatagat      180
tgacaagaaa ggttttttgcc aatccagaag actgtgtagc atttggcaaa ggagaaaatg    240
ccaagaagta tcttcgaaca gatgacagag tagaacgtgt acgcagagcc cacctgaatg     300
accttgaaaa tattattcca tttcttggaa ttggcctcct gtattccttg agtggtcccg     360
accccctcta agccatcctg cacttcagac tatttgtcgg agcacggatc taccacacca    420
ttgcatattt gacacccctt ccccagccaa atagagcttt gagttttttt gttggatatg    480
gagttactct ttccatggct tacaggttgc tgaaaagtaa attgtacctg taagaaaat    540 catacaactc agcatccagt tggcttttta agaattctgt acttccaatt tataatgaat    600
actttcttag attttaggta ggaggggagc agaggaatta tgaactgggg taaacccatt    660
ttgaatatta gcattgccaa tatcctgtat tcttgtttta catttggatt agaaatttaa    720
catagtaatt cttaagtctt ttgtctgatt tttaaagtac tttcttataa atttggatca    780
tgttatgatt tgtaacattc acacaacacc tcacttttga atctataaaa gaattgcacg    840
tatgagaaac ctatatttca atactgctga aacagacatg aaataaagaa tttaaagaat    900
gaaaaaaaaa aaaaaaaaa                                                  919

<210> SEQ ID NO 3
<211> LENGTH: 944
<212> TYPE: DNA
<213> ORGANISM: Homo Sapiens

<400> SEQUENCE: 3
acagtccctg cattgcgcgc gacccggcgg cgggacaggc ttgctgcttc ctcctcctcg      60
gcctcaccat tccagaccaa aattgaaaaa atggttgacc tcacccaggt aatggatgat    120
gaagtattca tggcttttgc atcctatgca acaattattc tttcaaaaat gatgcttatg    180
agtactgcaa ctgcattcta tagattgaca agaaaggttt ttgccaatcc agaagactgt    240
gtagcatttg gcaaggaga aaatgccaag aagtatcttc gaacagatga cagagtagaa    300
cgtgtacgca gagcccacct gaatgacctt gaaaatatta ttccatttct tggaattggc    360
ctcctgtatt ccttgagtgg tcccgacccc tctacagcca tcctgcactt cagactattt    420
gtcggagcac ggatctacca ccattgca tatttgacac cccttcccca gccaaataga    480
gctttgagtt ttttgttgg atatggagtt actctttcca tggcttacag gttgctgaaa    540
agtaaattgt acctgtaaag aaaatcatac aactcagcat ccagttggct ttttaagaat    600
tctgtacttc caatttataa tgaatacttt cttagatttt aggtaggagg ggagcagagg    660
aattatgaac tggggtaaac ccatttttgaa tattagcatt gccaatatcc tgtattcttg    720
ttttacattt ggattagaaa tttaacatag taattcttaa gtcttttgtc tgattttaa    780 agtactttct tataaatttg gatcatgtta tgatttgtaa cattcacaca acacctcact    840
tttgaatcta taaagaatt gcacgtatga gaaacctata tttcaatact gctgaaacag    900
acatgaaata aagaatttaa agaatgaaaa aaaaaaaaaaaa aaaa                    944

<210> SEQ ID NO 4
<211> LENGTH: 997
<212> TYPE: DNA
<213> ORGANISM: Homo Sapiens

<400> SEQUENCE: 4
ggcagatgga agacttgggg gggtctctgc cagctggaag tgcttggctc cacttagcag      60
```

```
ctaaacttag cttttcaatc gatcgctttt gaaagggaat tgtatttctg tccccgtgcg      120
gattccagac caaaattgaa aaatggttg acctcaccca ggtaatggat gatgaagtat       180
tcatggcttt tgcatcctat gcaacaatta ttctttcaaa aatgatgctt atgagtactg      240
caactgcatt ctatagattg acaagaaagg tttttgccaa tccagaagac tgtgtagcat      300
ttggcaaagg agaaaatgcc aagaagtatc ttcgaacaga tgacagagta gaacgtgtac      360
gcagagccca cctgaatgac cttgaaaata ttattccatt tcttggaatt ggcctcctgt      420
attccttgag tggtcccgac ccctctacag ccatcctgca cttcagacta tttgtcggag      480
cacggatcta ccacaccatt gcatatttga caccccttcc ccagccaaat agagctttga      540 gttttttgt tggatatgga gttactcttt ccatggctta caggttgctg aaaagtaaat       600
tgtacctgta aagaaaatca tacaactcag catccagttg cttttaag aattctgtac        660 ttccaattta taatgaatac tttcttagat tttaggtagg aggggagcag aggaattatg      720
aactggggta aacccatttt gaatattagc attgccaata tcctgtattc ttgttttaca      780
tttggattag aaatttaaca tagtaattct taagtctttt gtctgatttt taaagtactt      840
tcttataaat ttggatcatg ttatgatttg taacattcac acaacacctc acttttgaat      900 ctataaaga attgcacgta tgagaaacct atatttcaat actgctgaaa cagacatgaa       960
ataaagaatt taagaatga aaaaaaaaa aaaaaaa                                 997

<210> SEQ ID NO 5
<211> LENGTH: 927
<212> TYPE: DNA
<213> ORGANISM: Homo Sapiens

<400> SEQUENCE: 5
gaattcaagt cctaaagcct acagttttga atactactga aatgacaagt tattccagac       60
caaaattgaa aaatggttg acctcaccca ggtaatggat gatgaagtat tcatggcttt      120
tgcatcctat gcaacaatta ttctttcaaa aatgatgctt atgagtactg caactgcatt      180
ctatagattg acaagaaagg tttttgccaa tccagaagac tgtgtagcat ttggcaaagg      240
agaaaatgcc aagaagtatc ttcgaacaga tgacagagta gaacgtgtac gcagagccca      300
cctgaatgac cttgaaaata ttattccatt tcttggaatt ggcctcctgt attccttgag      360
tggtcccgac ccctctacag ccatcctgca cttcagacta tttgtcggag cacggatcta      420
ccacaccatt gcatatttga caccccttcc ccagccaaat agagctttga gttttttgt      480 tggatatgga gttactcttt ccatggctta caggttgctg aaaagtaaat tgtacctgta      540
aagaaaatca tacaactcag catccagttg cttttaag aattctgtac ttccaattta       600
taatgaatac tttcttagat tttaggtagg aggggagcag aggaattatg aactggggta      660
aacccatttt gaatattagc attgccaata tcctgtattc ttgttttaca tttggattag      720
aaatttaaca tagtaattct taagtctttt gtctgatttt taaagtactt tcttataaat      780
ttggatcatg ttatgatttg taacattcac acaacacctc acttttgaat ctataaaga       840 attgcacgta tgagaaacct atatttcaat actgctgaaa cagacatgaa ataaagaatt      900 taagaatga aaaaaaaaa aaaaaaa                                            927

<210> SEQ ID NO 6
<211> LENGTH: 937
<212> TYPE: DNA
<213> ORGANISM: Homo Sapiens

<400> SEQUENCE: 6
```

```
acagtccctg cattgcgcgc gacccggcgg cgggacaggc ttgctgcttc ctcctcctcg    60
gcctcaccac caaaattgaa aaaatggttg acctcaccca ggtaatggat gatgaagtat   120
tcatggcttt tgcatcctat gcaacaatta ttctttcaaa aatgatgctt atgagtactg   180
caactgcatt ctatagattg acaagaaagg ttttgccaa tccagaagac tgtgtagcat    240
ttggcaaagg agaaaatgcc aagaagtatc ttcgaacaga tgacagagta gaacgtgtac   300
gcagagccca cctgaatgac cttgaaaata ttattccatt tcttggaatt ggcctcctgt   360
attccttgag tggtcccgac ccctctacag ccatcctgca cttcagacta tttgtcggag   420
cacggatcta ccacaccatt gcatatttga caccccttcc ccagccaaat agagctttga   480
gttttttgt tggatatgga gttactcttt ccatggctta caggttgctg aaaagtaaat    540
tgtacctgta aagaaaatca tacaactcag catccagttg gcttttaag aattctgtac    600
ttccaattta taatgaatac tttcttagat tttaggtagg aggggagcag aggaattatg   660
aactggggta aacccatttt gaatattagc attgccaata tcctgtattc ttgttttaca   720
tttggattag aaatttaaca tagtaattct taagtctttt gtctgatttt taaagtactt   780
tcttataaat ttggatcatg ttatgatttg taacattcac acaacacctc acttttgaat   840
ctataaaaga attgcacgta tgagaaacct atatttcaat actgctgaaa cagacatgaa   900
ataaagaatt taagaatga aaaaaaaaa aaaaaaa                              937

<210> SEQ ID NO 7
<211> LENGTH: 1088
<212> TYPE: DNA
<213> ORGANISM: Homo Sapiens

<400> SEQUENCE: 7
acagtccctg cattgcgcgc gacccggcgg cgggacaggc ttgctgcttc ctcctcctcg    60
gcctcaccat tccagaccaa aattgaaaaa atggttgacc tcacccaggt aatggatgat   120
gaagtattca tggcttttgc atcctatgca acaattattc tttcaaaaat gatgcttatg   180
agtactgcaa ctgcattcta tagattgaca agaaaggttt tgccaatcc agaagactgt    240
gtagcatttg gcaaggaga aatgccaag aagtatcttc gaacagatga cagagtagaa    300
cgtgtacgca gtcattgtaa agctgttacg attagcatat ttgaacggca gagccagaat   360
ggggctacaa atgaagtgaa aagtatgctt taccgtgtgc aacaattgtg aaagttaata   420
catacacata tggaacaatt aactaaaaac ttaagagccc acctgaatga ccttgaaaat   480
attattccat ttcttggaat tggcctcctg tattccttga gtggtcccga cccctctaca   540
gccatcctgc acttcagact atttgtcgga gcacggatct accacaccat tgcatatttg   600
acacccttc cccagccaaa tagagctttg agtttttttg ttggatatgg agttactctt    660
tccatggctt acaggttgct gaaaagtaaa ttgtacctgt aaagaaaatc atacaactca   720
gcatccagtt ggcttttaa gaattctgta cttccaattt ataatgaata ctttcttaga    780
ttttaggtag gaggggagca gaggaattat gaactggggt aaacccattt tgaatattag   840
cattgccaat atcctgtatt cttgttttac atttggatta gaaatttaac atagtaattc   900
ttaagtcttt tgtctgattt ttaaagtact ttcttataaa tttggatcat gttatgattt   960
gtaacattca cacaacacct cacttttgaa tctataaaag aattgcacgt atgagaaacc  1020
tatatttcaa tactgctgaa acagacatga aataaagaat ttaagaatg aaaaaaaaaa  1080
aaaaaaaa                                                            1088
```

<210> SEQ ID NO 8
<211> LENGTH: 849
<212> TYPE: DNA
<213> ORGANISM: Homo Sapiens

<400> SEQUENCE: 8

| | | | | | |
|---|---|---|---|---|---|
| acagtccctg | cattgcgcgc | gacccggcgg | cgggacaggc | ttgctgcttc | ctcctcctcg | 60 |
| gcctcaccat | tccagaccaa | aattgaaaaa | atggttgacc | tcacccaggt | aatggatgat | 120 |
| gaagtattca | tggcttttgc | atcctatgca | acaattattc | tttcaaaaat | gatgcttatg | 180 |
| agtactgcaa | ctgcattcta | tagattgaca | agaaagagcc | cacctgaatg | accttgaaaa | 240 |
| tattattcca | tttcttggaa | ttggcctcct | gtattccttg | agtggtcccg | acccctctac | 300 |
| agccatcctg | cacttcagac | tatttgtcgg | agcacggatc | taccacacca | ttgcatattt | 360 |
| gacacccctt | ccccagccaa | atagagcttt | gagttttttt | gttggatatg | gagttactct | 420 |
| ttccatggct | tacaggttgc | tgaaaagtaa | attgtacctg | taaagaaaat | catacaactc | 480 |
| agcatccagt | tggcttttta | agaattctgt | acttccaatt | tataatgaat | actttcttag | 540 |
| attttaggta | ggaggggagc | agaggaatta | tgaactgggg | taaacccatt | ttgaatatta | 600 |
| gcattgccaa | tatcctgtat | tcttgtttta | catttggatt | agaaatttaa | catagtaatt | 660 |
| cttaagtctt | ttgtctgatt | tttaaagtac | tttcttataa | atttggatca | tgttatgatt | 720 |
| tgtaacattc | acacaacacc | tcactttga | atctataaaa | gaattgcacg | tatgagaaac | 780 |
| ctatatttca | atactgctga | aacagacatg | aaataaagaa | tttaaagaat | gaaaaaaaaa | 840 |
| aaaaaaaaa | | | | | | 849 |

<210> SEQ ID NO 9
<211> LENGTH: 1509
<212> TYPE: DNA
<213> ORGANISM: Homo Sapiens

<400> SEQUENCE: 9

| | | | | | |
|---|---|---|---|---|---|
| acagtccctg | cattgcgcgc | gacccggcgg | cgggacaggc | ttgctgcttc | ctcctcctcg | 60 |
| gcctcaccat | tccagaccaa | aattgaaaaa | atggttgacc | tcacccaggt | aatggatgat | 120 |
| gaagtattca | tggcttttgc | atcctatgca | acaattattc | tttcaaaaat | gatgcttatg | 180 |
| agtactgcaa | ctgcattcta | tagattgaca | agaaaggttt | ttgccaatcc | agaagactgt | 240 |
| gtagcatttg | gcaaaggaga | aaatgccaag | aagtatcttc | gaacagatga | cagagtagaa | 300 |
| cgtgtacgca | gaatcaaaca | aaccctgagc | atttatcttg | cctcttctat | ataaagttta | 360 |
| actcggcata | accaattgct | gatgaagaag | aaatgtttcc | ttgtagaagc | aaaccagtga | 420 |
| ataattgaag | aaaaaattta | tcttttcaac | atctaatgag | ttaatggatt | caagcaaaga | 480 |
| ttatccacgg | ctgttaacaa | cacaaaaaga | caatcggaaa | ttagctatta | ctgcgggaag | 540 |
| tacccaatac | catctatgaa | actgtgtgga | caaaaacact | gacaaaaatc | tccacgaatc | 600 |
| tctaattttg | aatacaaatt | taagaaaat | gcaaggaatt | aaaatagacc | atgatgaagt | 660 |
| cagaaaaatt | cagacagaga | aaatgctcc | aggaccagaa | acccatttct | tccgcaaaag | 720 |
| cttccaggta | gagattgact | gaccgagaga | acagagacat | agagagaacc | tagagattaa | 780 |
| aagaaacttg | agcgatttgt | cagcattcag | ttgcaacgta | tggatgtgat | ttgaattcta | 840 |
| atttaaaaac | caaagtagaa | agtggtaaac | aattggggaa | atgtgaacaa | tgatagaata | 900 |
| tttaatatta | atgaaatatg | ttaaatattt | tcagatatga | taatggcatt | gagtatgtaa | 960 |
| aaaagagcct | gttttaaag | aaatacctct | gaaatacaga | tgatataata | tcatctgtat | 1020 |

-continued

| | |
|---|---|
| attagatgat attatatata tcagtatcat cagaataaag taaggttagc atgaattgtt | 1080 |
| aattgttgac actgtgcaat aggtacgtgg ataattacta tactgttctc attccttttta | 1140 |
| tttatgtttg aaatgttcta aaattaaaag ttaaagcata gagtgtaaag ttgagcaaat | 1200 |
| tcctccaaga cctaaatata gcttatcaaa acttacatta attagatgct gactgttgag | 1260 |
| ctaatacttt ttttaatga tgtgtgcttc agtttattgc acttttcaaa tactccagtt | 1320 |
| ttttgtgtgc gtgtgttttt taaattttat tattattaaa gttttagggt acatgtgcaa | 1380 |
| aaaaaaaaaa aaaaaaaaa aaaaaaaaaa aaaaaaaaaa aaaaaaaaaa aaaaaaaaaa | 1440 |
| aaaaaaaaaa aaaaaaaaa aaaaaaaaaa aaaaaaaaaa aaaaaaaaaa aaaaaaaaaa | 1500 |
| aaaaaaaaa | 1509 |

<210> SEQ ID NO 10
<211> LENGTH: 902
<212> TYPE: DNA
<213> ORGANISM: Homo Sapiens

<400> SEQUENCE: 10

| | |
|---|---|
| ggcagatgga agacttgggg gggtctctgc cagctggaag tgcttggctc cacttagcag | 60 |
| ctaaacttag cttttcaatc gatcgctttt gaaagggaat tgtatttctg tccccgtgcg | 120 |
| gattccagac caaaattgaa aaaatggttg acctcaccca ggtaatggat gatgaagtat | 180 |
| tcatggcttt tgcatcctat gcaacaatta ttctttcaaa aatgatgctt atgagtactg | 240 |
| caactgcatt ctatagattg acaagaaaga gcccacctga atgaccttga aaatattatt | 300 |
| ccatttcttg gaattggcct cctgtattcc ttgagtggtc ccgacccctc tacagccatc | 360 |
| ctgcacttca gactatttgt cggagcacgg atctaccaca ccattgcata tttgacaccc | 420 |
| cttccccagc caaatagagc tttgagtttt tttgttggat atggagttac tctttccatg | 480 |
| gcttacaggt tgctgaaaag taaattgtac ctgtaaagaa aatcatacaa ctcagcatcc | 540 |
| agttggcttt ttaagaattc tgtacttcca atttataatg aatactttct tagatttttag | 600 |
| gtaggagggg agcagaggaa ttatgaactg gggtaaaccc atttttgaata ttagcattgc | 660 |
| caatatcctg tattcttgtt ttacatttgg attagaaatt taacatagta attcttaagt | 720 |
| cttttgtctg atttttaaag tactttctta taaatttgga tcatgttatg atttgtaaca | 780 |
| ttcacacaac acctcacttt tgaatctata aaagaattgc acgtatgaga aacctatatt | 840 |
| tcaatactgc tgaaacagac atgaaataaa gaatttaaag aatgaaaaaa aaaaaaaaa | 900 |
| aa | 902 |

<210> SEQ ID NO 11
<211> LENGTH: 1461
<212> TYPE: DNA
<213> ORGANISM: Homo Sapiens

<400> SEQUENCE: 11

| | |
|---|---|
| agatgcccca cagcactgct cttccagagg caagaccaac caagatgagt gccctgggag | 60 |
| ctgtcattgc cctcctgctc tggggacagc ttttttgcagt ggactcaggc aatgatgtca | 120 |
| cggatatcgc agatgacggc tgcccgaagc cccccgagat tgcacatggc tatgtggagc | 180 |
| actcggttcg ctaccagtgt aagaactact acaaactgcg cacagaagga gatggagtat | 240 |
| acacccttaaa tgataagaag cagtggataa ataaggctgt tggagataaa cttcctgaat | 300 |
| gtgaagcaga tgacggctgc ccgaagcccc ccgagattgc acatggctat gtggagcact | 360 |

|  |  |  |  |  |  |
|---|---|---|---|---|---|
| cggttcgcta | ccagtgtaag | aactactaca | aactgcgcac | agaaggagat | ggagtgtaca | 420 |
| ccttaaacaa | tgagaagcag | tggataaata | aggctgttgg | agataaactt | cctgaatgtg | 480 |
| aagcagtatg | tgggaagccc | aagaatccgg | caaacccagt | gcagcggatc | ctgggtggac | 540 |
| acctggatgc | caaaggcagc | tttcctggc | aggctaagat | ggtttcccac | cataatctca | 600 |
| ccacaggtgc | cacgctgatc | aatgaacaat | ggctgctgac | cacggctaaa | aatctcttcc | 660 |
| tgaaccattc | agaaaatgca | acagcgaaag | acattgcccc | tactttaaca | ctctatgtgg | 720 |
| ggaaaaagca | gcttgtagag | attgagaagg | ttgttctaca | ccctaactac | tcccaggtag | 780 |
| atattgggct | catcaaactc | aaacagaagg | tgtctgttaa | tgagagagtg | atgcccatct | 840 |
| gcctaccttc | aaaggattat | gcagaagtag | gcgtgtggg | ttatgttct | ggctggggc | 900 |
| gaaatgccaa | ttttaaattt | actgaccatc | tgaagtatgt | catgctgcct | gtggctgacc | 960 |
| aagaccaatg | cataaggcat | tatgaaggca | gcacagtccc | cgaaaagaag | acaccgaaga | 1020 |
| gccctgtagg | ggtgcagccc | atactgaatg | aacacacctt | ctgtgctggc | atgtctaagt | 1080 |
| accaagaaga | cacctgctat | ggcgatgcgg | gcagtgcctt | tgccgttcac | gacctggagg | 1140 |
| aggacacctg | gtatgcgact | gggatcttaa | gctttgataa | gagctgtgct | gtggctgagt | 1200 |
| atggtgtgta | tgtgaaggtg | acttccatcc | aggactgggg | tcagaagacc | atagctgaga | 1260 |
| actaatgcaa | ggctggccgg | aagcccttgc | ctgaaagcaa | gatttcagcc | tggaagaggg | 1320 |
| caaagtggac | gggagtggac | aggagtggat | gcgataagat | gtggtttgaa | gctgatgggt | 1380 |
| gccagccctg | cattgctgag | tcaatcaata | aagagctttc | ttttgaccca | taaaaaaaaa | 1440 |
| aaaaaaaaaa | aaaaaaaaaa | a |  |  |  | 1461 |

<210> SEQ ID NO 12
<211> LENGTH: 1284
<212> TYPE: DNA
<213> ORGANISM: Homo Sapiens

<400> SEQUENCE: 12

|  |  |  |  |  |  |  |
|---|---|---|---|---|---|---|
| agatgcccca | cagcactgct | cttccagagg | caagaccaac | caagatgagt | gccctgggag | 60 |
| ctgtcattgc | cctcctgctc | tggggacagc | tttttgcagt | ggactcaggc | aatgatgtca | 120 |
| cggatatcgc | agatgacggc | tgcccgaagc | cccccgagat | tgcacatggc | tatgtggagc | 180 |
| actcggttcg | ctaccagtgt | aagaactact | acaaactgcg | cacagaagga | gatggagtgt | 240 |
| acaccttaaa | caatgagaag | cagtggataa | ataaggctgt | tggagataaa | cttcctgaat | 300 |
| gtgaagcagt | atgtgggaag | cccaagaatc | cggcaaaccc | agtgcagcgg | atcctgggtg | 360 |
| gacacctgga | tgccaaaggc | agctttccct | ggcaggctaa | gatggtttcc | caccataatc | 420 |
| tcaccacagg | tgccacgctg | atcaatgaac | aatggctgct | gaccacggct | aaaaatctct | 480 |
| tcctgaacca | ttcagaaaat | gcaacagcga | aagacattgc | cctactttta | acactctatg | 540 |
| tggggaaaaa | gcagcttgta | gagattgaga | aggttgttct | acaccctaac | tactcccagg | 600 |
| tagatattgg | gctcatcaaa | ctcaaacaga | aggtgtctgt | taatgagaga | gtgatgccca | 660 |
| tctgcctacc | ttcaaaggat | tatgcagaag | tagggcgtgt | gggttatgtt | tctggctggg | 720 |
| ggcgaaatgc | caattttaaa | tttactgacc | atctgaagta | tgtcatgctg | cctgtggctg | 780 |
| accaagacca | atgcataagg | cattatgaag | gcagcacagt | ccccgaaaag | aagacaccga | 840 |
| agagccctgt | aggggtgcag | cccatactga | atgaacacac | cttctgtgct | ggcatgtcta | 900 |
| agtaccaaga | agacacctgc | tatggcgatg | cgggcagtgc | ctttgccgtt | cacgacctgg | 960 |
| aggaggacac | ctggtatgcg | actgggatct | taagctttga | taagagctgt | gctgtggctg | 1020 |

```
agtatggtgt gtatgtgaag gtgacttcca tccaggactg ggttcagaag accatagctg     1080
agaactaatg caaggctggc cggaagccct tgcctgaaag caagatttca gcctggaaga     1140
gggcaaagtg gacgggagtg gacaggagtg gatgcgataa gatgtggttt gaagctgatg     1200
ggtgccagcc ctgcattgct gagtcaatca ataaagagct ttcttttgac ccataaaaaa     1260
aaaaaaaaaa aaaaaaaaaa aaaa                                            1284

<210> SEQ ID NO 13
<211> LENGTH: 2787
<212> TYPE: DNA
<213> ORGANISM: Homo Sapiens

<400> SEQUENCE: 13
cctagtccca gcccagggggg ccgctctcgc cggcgtcgag ggcgtggcgg cgaggctgct      60
gctgcaggcg gctcccggct ctgccttcgg ccccgcccgc cgcccaccag gctcccagag     120
gccccgcagc tcgcgccgtc cggctcccgc cagcccgctc gggcagcccg gccccgtccg     180
ctgccctccc ggctcccgtc ctgcggcggc ggggcgtgca ggtgaggccc cacggcgccc     240
ggcctctcca gcagtgggtg cctgatagac atcctaggac tatacagaag gaaaaggccc     300
actttggggg ataatgctga gggacactat gaaatcttgg aatgatagcc agtcagatct     360
gtgtagcact gaccaagaag aggaagaaga gatgattttt ggtgaaaatg aagatgattt     420
ggatgagatg atggatttaa gtgatctgcc tacctcactt tttgcttgca gcgtccatga     480
agcagtgttt gaggcacgag agcagaagga aagatttgaa gcactcttca ccatctatga     540
tgaccaggtt acttttcagc tgtttaaaag ctttagaaga gtcagaataa atttcagcaa     600
acctgaagcg gcagcaagag cgcgaataga actccacgaa acagcttca atgggcagaa      660 gctaaagcta tatttgcac aggtgcagat gtccggcgaa gtgcgggaca agtcctatct      720
cctgccgccc cagcctgtca agcagttcct catctcccct ccagcctctc ccccggtggg     780
gtggaagcag agcgaagatg cgatgcctgt tataaattat gattactct gtgctgtttc      840 caaattggga ccaggagaga aatatgaact tcacgcggga acagagtcga cacccagcgt     900
ggtggttcat gtctgtgaaa gtgaaactga agaggaagaa gagacaaaaa accccaaaca     960
gaaaattgcc cagacgaggc gccccgaccc tccgaccgca gcgttgaatg agccccagac    1020
ctttgattgc gcgctgtgag gcccttggtt gtggtgcgag gcggctgccc tggtgggctc    1080
tggccatggc gctctgtgcc tgcggccgat gcgttgctgc aacagcata ggtgagactc     1140 tgccgagtga ggtataggtc ttctcaccac gcctgtactg cagacacggt cgtgtagagt    1200
agcagctgat ttgacctgtc ccagatttta agtgatattc caaagggac tttacattaa     1260 aggagaagcc cccaagatgt ggccacccctt aaccatttt aaatagtaac aaattaggaa    1320
aacagctccc ctcccctcca gccatgtaag tcctcctgat tctgtatcac atgagacacc    1380
aaaaactgga aatgtagtca cacccagtac agtaccattt ttatgaattt aaaaatagtc    1440 ttataattt aattgtttgt gggtattttt ctactggtat aaatagcttc taattaataa    1500
atcgatcaaa ggttgttact cagtatacat gaattttt gcaggaaaag aaaccagaaa     1560
tacagaataa ttcatagaaa tcatggttct caagtatttg ttcaattagc tttggggaag    1620
aaatgccaaa tccactttga ggatgagtct tacgacacag atccacccac atgttgctct    1680
tatctggaat ttgggacaaa gcaatgcaca ggccctcatt cctgatgtgg cgccctccag    1740
acatggctgc ccaggaagga cggccacttt agaagtggga cgtatcacca gtaagcttga    1800
```

| | |
|---|---|
| atgattagga tcgcaggtgg ctactgcatt ctgccgttcg tgaccgtgtt ctagcctgta | 1860 |
| gaccacccag ctaccttcat tcaccagttt ttatccttca ccttttccag tatcttgtta | 1920 |
| accactagtt cttgagtttt ttggctatga tgtgtacgtt tatgtatgtc attcatggac | 1980 |
| tttcaactag aaaaggtaat gataaggttt tctgaagacc atttgtaaat tgtccattta | 2040 |
| accattttc agcttgcttt gaaacaaaag tcacacctac tattttcta tgaattaggg | 2100 |
| aatgaggggg agatcattca gttttacttt tcttttttgtt gaaattttgt acccggattg | 2160 |
| cagttggcac ttttcctaaa acagaattgt ttcccactta ggtgtcagaa tgtacctttg | 2220 |
| aacttccta agaagcagca ggatcttttt aactctctct ggtctgttta gactttgaag | 2280 |
| tcccttctgt agaaaagtct cataactgag aaggctctgt tttgggccgg gtgggtctgc | 2340 |
| tggcctccac tcactgtgct gtttccttg agtggcacac ttgggaagct ccggggcatg | 2400 |
| tgaaggagct gcaaacatga gaactaatga accaaggcgg ctgccaccag gaaggaacag | 2460 |
| aacgcaggca ttcaaccatg acgtctgcac agtgttagta acatgtcatt gtggttttcgt | 2520 |
| tctcactgtg gtaaaattta tttctgagca cttaaactgt gttgcatacc cctaattttt | 2580 |
| ttttttctg tatcttcctt gccctcaaat accctgaggt gataaactgt tccagttgta | 2640 |
| gccaactacc actgctaggc ctcaatgtaa attcagttga aatttgcaat tctatcagca | 2700 |
| atttaatgta ttgaattcag atcatcattt gtcattttaa ccgacaacca cccaataaat | 2760 |
| ttactctgca gttctgaact caaaaaa | 2787 |

<210> SEQ ID NO 14
<211> LENGTH: 2754
<212> TYPE: DNA
<213> ORGANISM: Homo Sapiens

<400> SEQUENCE: 14

| | |
|---|---|
| cctagtccca gcccaggggg ccgctctcgc cggcgtcgag ggcgtggcgg cgaggctgct | 60 |
| gctgcaggcg gctcccggct ctgccttcgg ccccgcccgc cgcccaccag gctcccagag | 120 |
| gccccgcagc tcgcgccgtc cggctccccg cagcccgtc gggcagcccg ggcccgtccg | 180 |
| ctgccctccc ggctcccgtc ctgcggcggc ggggcgtgca gtgggtgcct gatagacatc | 240 |
| ctaggactat acagaaggaa aaggcccact ttgggggata atgctgaggg acactatgaa | 300 |
| atcttggaat gatagccagt cagatctgtg tagcactgac caagaagagg aagaagagat | 360 |
| gattttggt gaaatgaag atgatttgga tgagatgatg gatttaagtg atctgcctac | 420 |
| ctcactttt gcttgcagcg tccatgaagc agtgtttgag gcacgagagc agaaggaaag | 480 |
| atttgaagca ctcttcacca tctatgatga ccaggttact tttcagctgt ttaaaagctt | 540 |
| tagaagagtc agaataaatt tcagcaaacc tgaagcggca gcaagagcgc gaatagaact | 600 |
| ccacgaaaca gacttcaatg gcagaagct aaagctatat tttgcacagg tgcagatgtc | 660 |
| cggcgaagtg cgggacaagt cctatctcct gccgccccag cctgtcaagc agttcctcat | 720 |
| ctcccctcca gcctctcccc cggtggggtg gaagcagagc gaagatgcga tgcctgttat | 780 |
| aaattatgat ttactctgtg ctgttttccaa attgggacca ggagagaaat atgaacttca | 840 |
| cgcgggaaca gagtcgacac ccagcgtggt ggttcatgtc tgtgaaagtg aaactgaaga | 900 |
| ggaagaagag acaaaaaacc ccaaacagaa aattgcccag acgaggcgcc ccgaccctcc | 960 |
| gaccgcagcg ttgaatgagc cccagaccctt tgattgcgcg ctgtgaggcc cttggttgtg | 1020 |
| gtgcgaggcg gctgccctgg tgggctctgg ccatggcgct ctgtgcctgc ggccgatgcg | 1080 |
| ttgctgcgaa cagcataggt gagactctgc cgagtgaggt ataggtcttc tcaccacgcc | 1140 |

| | |
|---|---:|
| tgtactgcag acacggtcgt gtagagtagc agctgatttg acctgtccca gattttaagt | 1200 |
| gatattccaa aagggacttt acattaaagg agaagccccc aagatgtggc caccctta ac | 1260 |
| cattttta aa tagtaacaaa ttaggaaaac agctcccctc ccctccagcc atgtaagtcc | 1320 |
| tcctgattct gtatcacatg agacaccaaa aactggaaat gtagtcacac ccagtacagt | 1380 |
| accatttta tgaatttaaa aatagtctta taattttaat tgtttgtggg tattttctta | 1440 |
| ctggtataaa tagcttctaa ttaataaatc gatcaaaggt tgttactcag tatacatgaa | 1500 |
| atttttgca ggaaaagaaa ccagaaatac agaataattc atagaaatca tggttctcaa | 1560 |
| gtatttgttc aattagcttt ggggaagaaa tgccaaatcc actttgagga tgagtcttac | 1620 |
| gacacagatc cacccacatg ttgctcttat ctggaatttg gacaaagca atgcacaggc | 1680 |
| cctcattcct gatgtggcgc cctccagaca tggctgccca ggaaggacgg ccactttaga | 1740 |
| agtgggacgt atcaccagta agcttgaatg attaggatcg caggtggcta ctgcattctg | 1800 |
| ccgttcgtga ccgtgttcta gcctgtagac cacccagcta ccttcattca ccagttttta | 1860 |
| tccttcacct tttccagtat cttgttaacc actagttctt gagttttttg gctatgatgt | 1920 |
| gtacgtttat gtatgtcatt catggacttt caactagaaa aggtaatgat aaggttttct | 1980 |
| gaagaccatt tgtaaattgt ccatttaacc attttcagc ttgctttgaa acaaaagtca | 2040 |
| cacctactat ttttctatga attagggaat gaggggaga tcattcagtt ttactttct | 2100 |
| ttttgttgaa atttttgtacc cggattgcag ttggcacttt tcctaaaaca gaattgtttc | 2160 |
| ccacttaggt gtcagaatgt acctttgaac ttccctaaga agcagcagga tctttttaac | 2220 |
| tctctctggt ctgtttagac tttgaagtcc cttctgtaga aaagtctcat aactgagaag | 2280 |
| gctctgtttt gggccgggtg ggtctgctgg cctccactca ctgtgctgtt tcctttgagt | 2340 |
| ggcacacttg ggaagctccg gggcatgtga aggagctgca acatgagaa ctaatgaacc | 2400 |
| aaggcggctg ccaccaggaa ggaacagaac gcaggcattc aaccatgacg tctgcacagt | 2460 |
| gttagtaaca tgtcattgtg gtttcgttct cactgtggta aaatttattt ctgagcactt | 2520 |
| aaactgtgtt gcatacccct aattttttt ttttctgtat cttccttgcc ctcaaatacc | 2580 |
| ctgaggtgat aaactgttcc agttgtagcc aactaccact gctaggcctc aatgtaaatt | 2640 |
| cagttgaaat ttgcaattct atcagcaatt taatgtattg aattcagatc atcatttgtc | 2700 |
| attttaaccg acaaccaccc aataaattta ctctgcagtt ctgaactcaa aaaa | 2754 |

<210> SEQ ID NO 15
<211> LENGTH: 2668
<212> TYPE: DNA
<213> ORGANISM: Homo Sapiens

<400> SEQUENCE: 15

| | |
|---|---:|
| gtaagagcta agtccacctg acaactttgt cttgaagaaa agattaatga aagccacagt | 60 |
| gagatacact gtcactccct gccccgcttc cgcagggccc cttccagat tggagatttc | 120 |
| tggcacgata aatgatgggt gcctgataga catcctagga ctatacagaa ggaaaaggcc | 180 |
| cactttgggg gataatgctg agggacacta tgaaatcttg gaatgatagc cagtcagatc | 240 |
| tgtgtagcac tgaccaagaa gaggaagaag agatgatttt tggtgaaaat gaagatgatt | 300 |
| tggatgagat gatggattta agtgatctgc ctacctcact ttttgcttgc agcgtccatg | 360 |
| aagcagtgtt tgaggcacga gagcagaagg aaagatttga agcactcttc accatctatg | 420 |
| atgaccaggt tactttcag ctgttaaaa gctttagaag agtcagaata aatttcagca | 480 |

-continued

| | |
|---|---|
| aacctgaagc ggcagcaaga gcgcgaatag aactccacga aacagacttc aatgggcaga | 540 |
| agctaaagct atattttgca caggtgcaga tgtccggcga agtgcgggac aagtcctatc | 600 |
| tcctgccgcc ccagcctgtc aagcagttcc tcatctcccc tccagcctct ccccggtgg | 660 |
| ggtggaagca gagcgaagat gcgatgcctg ttataaatta tgatttactc tgtgctgttt | 720 |
| ccaaattggg accaggagag aaatatgaac ttcacgcggg aacagagtcg acacccagcg | 780 |
| tggtggttca tgtctgtgaa agtgaaactg aagaggaaga agagacaaaa accccaaac | 840 |
| agaaaattgc ccagacgagg cgccccgacc ctccgaccgc agcgttgaat gagccccaga | 900 |
| cctttgattg cgcgctgtga ggcccttggt tgtggtgcga ggcggctgcc ctggtgggct | 960 |
| ctggccatgg cgctctgtgc ctgcggccga tgcgttgctg cgaacagcat aggtgagact | 1020 |
| ctgccgagtg aggtataggt cttctcacca cgcctgtact gcagacacgg tcgtgtagag | 1080 |
| tagcagctga tttgacctgt cccagatttt aagtgatatt ccaaagggga ctttacatta | 1140 |
| aaggagaagc ccccaagatg tggccaccct aaccatttt taaatagtaa caaattagga | 1200 |
| aaacagctcc cctcccctcc agccatgtaa gtcctcctga ttctgtatca catgagacac | 1260 |
| caaaaactgg aaatgtagtc acacccagta cagtaccatt tttatgaatt taaaaatagt | 1320 |
| cttataattt taattgtttg tgggtatttt tctactggta taaatagctt ctaattaata | 1380 |
| aatcgatcaa aggttgttac tcagtataca tgaaattttt tgcaggaaaa gaaaccagaa | 1440 |
| atacagaata attcatagaa atcatggttc tcaagtattt gttcaattag ctttggggaa | 1500 |
| gaaatgccaa atccactttg aggatgagtc ttacgacaca gatccaccca catgttgctc | 1560 |
| ttatctggaa tttgggacaa agcaatgcac aggccctcat tcctgatgtg gcgccctcca | 1620 |
| gacatggctg cccaggaagg acggccactt tagaagtggg acgtatcacc agtaagcttg | 1680 |
| aatgattagg atcgcaggtg gctactgcat tctgccgttc gtgaccgtgt tctagcctgt | 1740 |
| agaccaccca gctaccttca ttccagtt tttatccttc accttttcca gtatcttgtt | 1800 |
| aaccactagt tcttgagttt tttggctatg atgtgtacgt ttatgtatgt cattcatgga | 1860 |
| ctttcaacta gaaaaggtaa tgataaggtt ttctgaagac catttgtaaa ttgtccattt | 1920 |
| aaccattttt cagcttgctt tgaaacaaaa gtcacaccta ctattttct atgaattagg | 1980 |
| gaatgagggg gagatcattc agttttactt ttcttttgt tgaaattttg tacccggatt | 2040 |
| gcagttggca cttttcctaa aacagaattg tttcccactt aggtgtcaga atgtacctt | 2100 |
| gaacttccct aagaagcagc aggatctttt taactctctc tggtctgttt agactttgaa | 2160 |
| gtcccttctg tagaaaagtc tcataactga gaaggctctg ttttgggccg ggtgggtctg | 2220 |
| ctggcctcca ctcactgtgc tgtttccttt gagtggcaca cttgggaagc tccggggcat | 2280 |
| gtgaaggagc tgcaaacatg agaactaatg aaccaaggcg gctgccacca ggaaggaaca | 2340 |
| gaacgcaggc attcaaccat gacgtctgca cagtgttagt aacatgtcat tgtggtttcg | 2400 |
| ttctcactgt ggtaaaattt atttctgagc acttaaactg tgttgcatac ccctaatttt | 2460 |
| ttttttttct gtatcttcct tgccctcaaa taccctgagg tgataaactg ttccagttgt | 2520 |
| agccaactac cactgctagg cctcaatgta aattcagttg aaatttgcaa ttctatcagc | 2580 |
| aatttaatgt attgaattca gatcatcatt tgtcatttta accgacaacc acccaataaa | 2640 |
| tttactctgc agttctgaac tcaaaaaa | 2668 |

<210> SEQ ID NO 16
<211> LENGTH: 2646
<212> TYPE: DNA
<213> ORGANISM: Homo Sapiens

<400> SEQUENCE: 16

```
gtgctagctc cagctcagct acctgcggcc gcctctcctc gggcaatgag gcgccgggaa        60
gcccacagca tctgataata tccgggccgc cggttgccgg gaggtgaacc gagtgggtgc       120
ctgatagaca tcctaggact atacagaagg aaaaggccca ctttgggggga taatgctgag      180
ggacactatg aaatcttgga atgatagcca gtcagatctg tgtagcactg accaagaaga       240
ggaagaagag atgattttg gtgaaaatga agatgatttg gatgagatga tggatttaag        300
tgatctgcct acctcacttt ttgcttgcag cgtccatgaa gcagtgtttg aggcacgaga       360
gcagaaggaa agatttgaag cactcttcac catctatgat gaccaggtta cttttcagct       420
gtttaaaagc tttagaagag tcagaataaa tttcagcaaa cctgaagcgg cagcaagagc      480
gcgaatagaa ctccacgaaa cagacttcaa tgggcagaag ctaaagctat attttgcaca      540
ggtgcagatg tccggcgaag tgcgggacaa gtcctatctc ctgccgcccc agcctgtcaa      600
gcagttcctc atctcccctc cagcctctcc cccggtgggg tggaagcaga gcgaagatgc      660
gatgcctgtt ataaattatg atttactctg tgctgtttcc aaattgggac caggagagaa      720
atatgaactt cacgcgggaa cagagtcgac acccagcgtg gtggttcatg tctgtgaaag      780
tgaaactgaa gaggaagaag agacaaaaaa ccccaaacag aaaattgccc agacgaggcg      840
ccccgaccct ccgaccgcag cgttgaatga gccccagacc tttgattgcg cgctgtgagg      900
cccttggttg tggtgcgagg cggctgccct ggtgggctct ggccatggcg ctctgtgcct      960
gcggccgatg cgttgctgcg aacagcatag gtgagactct gccgagtgag gtataggtct     1020
tctcaccacg cctgtactgc agacacggtc gtgtagagta gcagctgatt tgacctgtcc     1080
cagattttaa gtgatattcc aaagggact ttacattaaa ggagaagccc caagatgtg       1140
gccacccttaa ccattttta aatagtaaca aattaggaaa acagctcccc tcccctccag     1200
ccatgtaagt cctcctgatt ctgtatcaca tgagacacca aaaactggaa atgtagtcac     1260
acccagtaca gtaccatttt tatgaattta aaaatagtct tataattta attgtttgtg      1320
ggtattttc tactggtata aatagcttct aattaataaa tcgatcaaag gttgttactc     1380
agtatacatg aaattttttg caggaaaaga aaccagaaat acagaataat tcatagaaat     1440
catggttctc aagtatttgt tcaattagct ttggggaaga aatgccaaat ccactttgag     1500
gatgagtctt acgacacaga tccacccaca tgttgctctt atctggaatt tgggacaaag     1560
caatgcacag gccctcattc ctgatgtggc gccctccaga catggctgcc caggaaggac     1620
ggccacttta gaagtgggac gtatcaccag taagcttgaa tgattaggat cgcaggtggc     1680
tactgcattc tgccgttcgt gaccgtgttc tagcctgtag accacccagc taccttcatt     1740
caccagtttt tatccttcac ctttttccagt atcttgttaa ccactagttc ttgagttttt     1800
tggctatgat gtgtacgttt atgtatgtca ttcatggact ttcaactaga aaaggtaatg     1860
ataaggtttt ctgaagacca tttgtaaatt gtccatttaa ccattttcca gcttgctttg     1920
aaacaaaagt cacacctact attttctat gaattaggga atgaggggga gatcattcag      1980
ttttacttt cttttttgttg aaatttttgta cccggattgc agttggcact tttcctaaaa     2040
cagaattgtt tccacttag gtgtcagaat gtaccttga acttccctaa gaagcagcag       2100
gatcttttta actctctctg gtctgtttag actttgaagt cccttctgta gaaaagtctc     2160
ataactgaga aggctctgtt ttgggccggg tgggtctgct ggcctccact cactgtgctg      2220
tttcctttga gtggcacact tgggaagctc cggggcatgt gaaggagctg caaacatgag      2280
```

```
aactaatgaa ccaaggcggc tgccaccagg aaggaacaga acgcaggcat tcaaccatga    2340
cgtctgcaca gtgttagtaa catgtcattg tggtttcgtt ctcactgtgg taaaatttat    2400
ttctgagcac ttaaactgtg ttgcataccc ctaattttt ttttttctgt atcttccttg     2460
ccctcaaata ccctgaggtg ataaactgtt ccagttgtag ccaactacca ctgctaggcc    2520
tcaatgtaaa ttcagttgaa atttgcaatt ctatcagcaa tttaatgtat tgaattcaga    2580
tcatcatttg tcattttaac cgacaaccac ccaataaatt tactctgcag ttctgaactc    2640
aaaaaa                                                               2646
```

<210> SEQ ID NO 17
<211> LENGTH: 2503
<212> TYPE: DNA
<213> ORGANISM: Homo Sapiens

<400> SEQUENCE: 17

```
tgggtgcctg atagacatcc taggactata cagaaggaaa aggcccactt tgggggataa     60
tgctgaggga cactatgaaa tcttggaatg atagccagtc agatctgtgt agcactgacc    120
aagaagagga agaagagatg atttttggtg aaaatgaaga tgatttggat gagatgatgg    180
atttaagtga tctgcctacc tcacttttg cttgcagcgt ccatgaagca gtgtttgagg     240
cacgagagca gaaggaaaga tttgaagcac tcttcaccat ctatgatgac caggttactt    300
ttcagctgtt taaaagcttt agaagagtca gaataaattt cagcaaacct gaagcggcag    360
caagagcgcg aatagaactc cacgaaacag acttcaatgg gcagaagcta agctatatt    420 ttgcacagtc ctatctcctg ccgccccagc ctgtcaagca gttcctcatc tcccctccag    480
cctctccccc ggtggggtgg aagcagagcg aagatgcgat gcctgttata aattatgatt    540
tactctgtgc tgtttccaaa ttgggaccag agagaaata tgaacttcac gcgggaacag    600
agtcgacacc cagcgtggtg gttcatgtct gtgaaagtga aactgaagag gaagaagaga    660
caaaaaaccc caaacagaaa attgcccaga cgaggcgccc cgaccctccg accgcagcgt    720
tgaatgagcc ccagaccttt gattgcgcgc tgtgaggccc ttggttgtgg tgcgaggcgg    780
ctgccctggt gggctctggc catggcgctc tgtgcctgcg gccgatgcgt tgctgcgaac    840
agcataggtg agactctgcc gagtgaggta taggtcttct caccacgcct gtactgcaga    900
cacggtcgtg tagagtagca gctgatttga cctgtcccag attttaagtg atattccaaa    960
agggacttta cattaaagga gaagccccca agatgtggcc acccttaacc attttttaaat   1020 agtaacaaat taggaaaaca gctcccctcc cctccagcca tgtaagtcct cctgattctg    1080
tatcacatga gacaccaaaa actggaaatg tagtcacacc cagtacagta ccattttat    1140 gaatttaaaa atagtcttat aattttaatt gtttgtgggt attttctac tggtataaat     1200 agcttctaat taataaatcg atcaaaggtt gttactcagt atacatgaaa ttttttgcag    1260
gaaaagaaac cagaaataca gaataattca tagaaatcat ggttctcaag tatttgttca    1320
attagctttg gggaagaaat gccaaatcca ctttgaggat gagtcttacg acacagatcc    1380
acccacatgt tgctcttatc tggaatttgg gacaaagcaa tgcacaggcc ctcattcctg    1440
atgtggcgcc ctccagacat ggctgcccag gaaggacggc cactttagaa gtgggacgta    1500
tcaccagtaa gcttgaatga ttaggatcgc aggtggctac tgcattctgc cgttcgtgac    1560
cgtgttctag cctgtagacc acccagctac cttcattcac cagttttat ccttcacctt     1620 ttccagtatc ttgttaacca ctagttcttg agttttttgg ctatgatgtg tacgtttatg    1680
tatgtcattc atggactttc aactagaaaa ggtaatgata aggttttctg aagaccattt    1740
```

-continued

| | |
|---|---|
| gtaaattgtc catttaacca tttttcagct tgctttgaaa caaaagtcac acctactatt | 1800 |
| tttctatgaa ttagggaatg aggggggagat cattcagttt tacttttctt tttgttgaaa | 1860 |
| ttttgtaccc ggattgcagt tggcactttt cctaaaacag aattgtttcc cacttaggtg | 1920 |
| tcagaatgta cctttgaact tccctaagaa gcagcaggat ctttttaact ctctctggtc | 1980 |
| tgtttagact ttgaagtccc ttctgtagaa aagtctcata actgagaagg ctctgttttg | 2040 |
| ggccgggtgg gtctgctggc ctccactcac tgtgctgttt cctttgagtg gcacacttgg | 2100 |
| gaagctccgg ggcatgtgaa ggagctgcaa acatgagaac taatgaacca aggcggctgc | 2160 |
| caccaggaag gaacagaacg caggcattca accatgacgc tgcacagtg ttagtaacat | 2220 |
| gtcattgtgg tttcgttctc actgtggtaa aatttatttc tgagcactta aactgtgttg | 2280 |
| cataccccta attttttttt tttctgtatc ttccttgccc tcaaataccc tgaggtgata | 2340 |
| aactgttcca gttgtagcca actaccactg ctaggcctca atgtaaattc agttgaaatt | 2400 |
| tgcaattcta tcagcaattt aatgtattga attcagatca tcatttgtca ttttaaccga | 2460 |
| caaccaccca ataaatttac tctgcagttc tgaactcaaa aaa | 2503 |

```
<210> SEQ ID NO 18
<211> LENGTH: 2580
<212> TYPE: DNA
<213> ORGANISM: Homo Sapiens

<400> SEQUENCE: 18
```

| | |
|---|---|
| cctagtccca gcccaggggg ccgctctcgc cggcgtcgag ggcgtggcgg cgaggctgct | 60 |
| gctgcaggcg gctcccggct ctgccttcgg ccccgcccgc cgcccaccag gctcccagag | 120 |
| gccccgcagc tcgcgccgtc cggctccccg cagccccgtc gggcagcccg ggcccgtccg | 180 |
| ctgccctccc ggctcccgtc ctgcggcggc ggggcgtgca gtgggtgcct gatagacatc | 240 |
| ctaggactat acagaaggaa aaggcccact ttgggggata atgctgaggg cactatgaa | 300 |
| atcttggaat gatagccagt cagatctgtg tagcactgac caagaagagg aagaagagat | 360 |
| gattttggt gaaaatgaag atgatttgga tgagatgatg gatttaagtg atctgcctac | 420 |
| ctcactttt gcttgcagcg tccatgaagc agtgtttgag gcacgagagc agaaggtgca | 480 |
| gatgtccggc gaagtgcggg acaagtccta tctcctgccg ccccagcctg tcaagcagtt | 540 |
| cctcatctcc cctccagcct ctcccccggt ggggtggaag cagagcgaag atgcgatgcc | 600 |
| tgttataaat tatgatttac tctgtgctgt ttccaaattg ggaccaggag agaaatatga | 660 |
| acttcacgcg ggaacagagt cgacacccag cgtggtggtt catgtctgtg aaagtgaaac | 720 |
| tgaagaggaa gaagagacaa aaaacccaa acagaaaatt gcccagacga ggcgcccga | 780 |
| ccctccgacc gcagcgttga atgagcccca gacctttgat tgcgcgctgt gaggcccttg | 840 |
| gttgtggtgc gaggcggctg ccctggtggg ctctggccat ggcgctctgt gcctgcggcc | 900 |
| gatgcgttgc tgcgaacagc ataggtgaga ctctgccgag tgaggtatag gtcttctcac | 960 |
| cacgcctgta ctgcagacac ggtcgtgtag agtagcagct gatttgacct gtcccagatt | 1020 |
| ttaagtgata ttccaaaagg gactttacat taaaggagaa gccccaagaa tgtggccacc | 1080 |
| cttaaccatt tttaaatagt aacaaattag gaaaacagct cccctcccct ccagccatgt | 1140 |
| aagtcctcct gattctgtat cacatgagac accaaaaact ggaaatgtag tcacacccag | 1200 |
| tacagtacca tttttatgaa tttaaaaata gtcttataat tttaattgtt tgtgggtatt | 1260 |
| tttctactgg tataaatagc ttctaattaa taaatcgatc aaaggttgtt actcagtata | 1320 |

```
catgaaattt tttgcaggaa agaaaccag aaatacagaa taattcatag aaatcatggt    1380
tctcaagtat ttgttcaatt agctttgggg aagaaatgcc aaatccactt tgaggatgag    1440
tcttacgaca cagatccacc cacatgttgc tcttatctgg aatttgggac aaagcaatgc    1500
acaggccctc attcctgatg tggcgccctc cagacatggc tgcccaggaa ggacggccac    1560
tttagaagtg ggacgtatca ccagtaagct tgaatgatta ggatcgcagg tggctactgc    1620
attctgccgt tcgtgaccgt gttctagcct gtagaccacc cagctacctt cattcaccag    1680
tttttatcct tcaccttttc cagtatcttg ttaaccacta gttcttgagt ttttggcta    1740 tgatgtgtac gttatgtat gtcattcatg gactttcaac tagaaaaggt aatgataagg    1800
ttttctgaag accatttgta aattgtccat ttaaccattt ttcagcttgc tttgaaacaa    1860
aagtcacacc tactattttt ctatgaatta gggaatgagg gggagatcat tcagttttac    1920
ttttcttttt gttgaaattt tgtacccgga ttgcagttgg cacttttcct aaaacagaat    1980
tgtttcccac ttaggtgtca gaatgtacct ttgaacttcc ctaagaagca gcaggatctt    2040
tttaactctc tctggtctgt ttagactttg aagtcccttc tgtagaaaag tctcataact    2100
gagaaggctc tgttttgggc cgggtgggtc tgctggcctc cactcactgt gctgtttcct    2160
ttgagtggca cacttgggaa gctccggggc atgtgaagga gctgcaaaca tgagaactaa    2220
tgaaccaagg cggctgccac caggaaggaa cagaacgcag gcattcaacc atgacgtctg    2280
cacagtgtta gtaacatgtc attgtggttt cgttctcact gtggtaaaat ttatttctga    2340
gcacttaaac tgtgttgcat acccctaatt ttttttttt ctgtatcttc cttgccctca    2400
aataccctga ggtgataaac tgttccagtt gtagccaact accactgcta ggcctcaatg    2460
taaattcagt tgaaatttgc aattctatca gcaatttaat gtattgaatt cagatcatca    2520
tttgtcattt taaccgacaa ccacccaata aatttactct gcagttctga actcaaaaaa    2580
```

<210> SEQ ID NO 19
<211> LENGTH: 2361
<212> TYPE: DNA
<213> ORGANISM: Homo Sapiens

<400> SEQUENCE: 19

```
tgggtgcctg atagacatcc taggactata cagaaggaaa aggcccactt tgggggataa      60
tgctgaggga cactatgaaa tcttggaatg atagccagtc agatctgtgt agcactgacc     120
aagaagagga agaagagatg attttggtg aaaatgaaga tgatttggat gagatgatgg     180
atttaagtga tctgcctacc tcactttttg cttgcagcgt ccatgaagca gtgtttgagg     240
cacgagagca gaaggaaaga tttgaagcac tcttcaccat ctatgatgac caggttactt     300
ttcagctgtt taaaagcttt agaagagtca gaataaattt cagcaaacct gaagcggcag     360
caagagcgcg aatagaactc cacgaaacag acttcaatgg gcagaagcta aagctatatt     420
ttgcacagga gagaaatatg aacttcacgc gggaacagag tcgacaccca gcgtggtggt     480
tcatgtctgt gaaagtgaaa ctgaagagga agaagagaca aaaaccccca aacagaaaat     540
tgcccagacg aggcgccccg accctccgac cgcagcgttg aatgagcccc agacctttga     600
ttgcgcgctg tgaggccctt ggttgtggtg cgaggcggct gccctggtgg gctctggcca     660
tggcgctctg tgcctgcggc cgatgcgttg ctgcgaacag cataggtgag actctgccga     720
gtgaggtata ggtcttctca ccacgcctgt actgcagaca cggtcgtgta gagtagcagc     780
tgatttgacc tgtcccagat tttaagtgat attccaaaag ggactttaca ttaaaggaga     840
agcccccaag atgtggccac ccttaaccat ttttaaatag taacaaatta ggaaaacagc     900
```

```
tcccctcccc tccagccatg taagtcctcc tgattctgta tcacatgaga caccaaaaac    960
tggaaatgta gtcacaccca gtacagtacc attttatga atttaaaaat agtcttataa   1020
ttttaattgt ttgtgggtat ttttctactg gtataaatag cttctaatta ataaatcgat   1080
caaaggttgt tactcagtat acatgaaatt ttttgcagga aaagaaacca gaaatacaga   1140
ataattcata gaaatcatgg ttctcaagta tttgttcaat tagctttggg aagaaatgc    1200 caaatccact tgaggatga gtcttacgac acagatccac ccacatgttg ctcttatctg    1260
gaatttggga caaagcaatg cacaggccct cattcctgat gtggcgccct ccagacatgg   1320
ctgcccagga aggacggcca ctttagaagt gggacgtatc accagtaagc ttgaatgatt   1380
aggatcgcag gtggctactg cattctgccg ttcgtgaccg tgttctagcc tgtagaccac   1440
ccagctacct tcattcacca gttttatcc ttcacctttt ccagtatctt gttaaccact    1500
agttcttgag ttttttggct atgatgtgta cgtttatgta tgtcattcat ggactttcaa   1560
ctagaaaagg taatgataag gttttctgaa gaccatttgt aaattgtcca tttaaccatt   1620
tttcagcttg cttgaaaca aaagtcacac ctactatttt tctatgaatt agggaatgag    1680
ggggagatca ttcagtttta cttttctttt tgttgaaatt ttgtacccgg attgcagttg   1740
gcacttttcc taaaacagaa ttgtttccca cttaggtgtc agaatgtacc tttgaacttc   1800
cctaagaagc agcaggatct ttttaactct ctctggtctg tttagacttt gaagtccctt   1860
ctgtagaaaa gtctcataac tgagaaggct ctgttttggg ccgggtgggt ctgctggcct   1920
ccactcactg tgctgtttcc tttgagtggc acacttggga agctccgggg catgtgaagg   1980
agctgcaaac atgagaacta atgaaccaag gcggctgcca ccaggaagga acagaacgca   2040
ggcattcaac catgacgtct gcacagtgtt agtaacatgt cattgtggtt tcgttctcac   2100
tgtggtaaaa tttatttctg agcacttaaa ctgtgttgca taccctaat tttttttttt    2160 tctgtatctt ccttgccctc aaatacctt aggtgataaa ctgttccagt tgtagccaac    2220
taccactgct aggcctcaat gtaaattcag ttgaaatttg caattctatc agcaatttaa   2280
tgtattgaat tcagatcatc atttgtcatt ttaaccgaca accacccaat aaatttactc   2340
tgcagttctg aactcaaaaa a                                             2361

<210> SEQ ID NO 20
<211> LENGTH: 2533
<212> TYPE: DNA
<213> ORGANISM: Homo Sapiens

<400> SEQUENCE: 20
cctagtccca gcccagggg ccgctctcgc cggcgtcgag ggcgtggcgg cgaggctgct     60
gctgcaggcg gctcccggct ctgccttcgg ccccgcccgc cgcccaccag gctcccagag   120
gccccgcagc tcgcgccgtc cggctccccg cagcccgtc gggcagcccg gcccgtccg    180 ctgccctccc ggctcccgtc ctgcggcgg ggggcgtgca ggtgaggccc cacggcgccc    240
ggcctctcca gcaggaaaga tttgaagcac tcttcaccat ctatgatgac caggttactt   300
ttcagctgtt taaaagcttt agaagagtca gaataaattt cagcaaacct gaagcggcag   360
caagagcgcg aatagaactc cacgaaacag acttcaatgg gcagaagcta aagctatatt   420
ttgcacaggt gcagatgtcc ggcgaagtgc gggacaagtc ctatctcctg ccgccccagc   480
ctgtcaagca gttcctcatc tcccctccag cctctccccc ggtggggtgg aagcagagcg   540
aagatgcgat gcctgttata aattatgatt tactctgtgc tgtttccaaa ttgggaccag   600
```

```
gagagaaata tgaacttcac gcgggaacag agtcgacacc cagcgtggtg gttcatgtct      660
gtgaaagtga aactgaagag gaagaagaga caaaaaaccc caaacagaaa attgcccaga      720
cgaggcgccc cgaccctccg accgcagcgt tgaatgagcc ccagacccttt gattgcgcgc     780 tgtgaggccc ttggttgtgg tgcgaggcgg ctgccctggt gggctctggc catggcgctc     840
tgtgcctgcg gccgatgcgt tgctgcgaac agcataggtg agactctgcc gagtgaggta     900
taggtcttct caccacgcct gtactgcaga cacggtcgtg tagagtagca gctgatttga     960
cctgtcccag attttaagtg atattccaaa agggacttta cattaaagga gaagccccca    1020
agatgtggcc acccttaacc atttttaaat agtaacaaat taggaaaaca gctcccctcc    1080
cctccagcca tgtaagtcct cctgattctg tatcacatga gacaccaaaa actggaaatg    1140
tagtcacacc cagtcagta ccattttttat gaatttaaaa atagtcttat aattttaatt     1200
gtttgtgggt attttttctac tggtataaat agcttctaat taataaatcg atcaaaggtt    1260
gttactcagt atacatgaaa ttttttgcag gaaaagaaac cagaaataca gaataattca    1320
tagaaatcat ggttctcaag tatttgttca attagctttg gggaagaaat gccaaatcca    1380
ctttgaggat gagtcttacg acacagatcc acccacatgt tgctcttatc tggaatttgg    1440
gacaaagcaa tgcacaggcc ctcattcctg atgtggcgcc ctccagacat ggctgcccag    1500
gaaggacggc cactttagaa gtgggacgta tcaccagtaa gcttgaatga ttaggatcgc    1560
aggtggctac tgcattctgc cgttcgtgac cgtgttctag cctgtagacc cccagctac    1620 cttcattcac cagttttat ccttcacctt ttccagtatc ttgttaacca ctagttcttg     1680
agttttttgg ctatgatgtg tacgtttatg tatgtcattc atggactttc aactagaaaa    1740
ggtaatgata aggttttctg aagaccattt gtaaattgtc catttaacca ttttttcagct   1800 tgctttgaaa caaagtcac acctactatt tttctatgaa ttagggaatg agggggagat     1860
cattcagttt tacttttctt tttgttgaaa ttttgtaccc ggattgcagt tggcactttt    1920
cctaaaacag aattgtttcc cacttaggtg tcagaatgta ccttttgaact tccctaagaa    1980 gcagcaggat cttttttaact ctctctggtc tgtttagact ttgaagtccc ttctgtagaa    2040
aagtctcata actgagaagg ctctgttttg ggccgggtgg gtctgctggc ctccactcac    2100
tgtgctgttt cctttgagtg gcacacttgg gaagctccgg ggcatgtgaa ggagctgcaa    2160
acatgagaac taatgaacca aggcggctgc caccaggaag gaacagaacg caggcattca    2220
accatgacgt ctgcacagtg ttagtaacat gtcattgtgg tttcgttctc actgtggtaa    2280
aatttatttc tgagcactta aactgtgttg cataccccta atttttttttt tttctgtatc   2340 ttccttgccc tcaaataccc tgaggtgata aactgttcca gttgtagcca actaccactg    2400
ctaggcctca atgtaaattc agttgaaatt tgcaattcta tcagcaattt aatgtattga    2460
attcagatca tcatttgtca ttttaaccga caaccaccca ataaatttac tctgcagttc    2520
tgaactcaaa aaa                                                       2533
```

<210> SEQ ID NO 21
<211> LENGTH: 2392
<212> TYPE: DNA
<213> ORGANISM: Homo Sapiens

<400> SEQUENCE: 21

```
gtgctagctc cagctcagct acctgcggcc gcctctcctc gggcaatgag gcgccgggaa      60
gcccacagca tctgataata tccgggccgc cggttgccgg gaggtgaacc gaggaaagat     120
ttgaagcact cttccaccatc tatgatgacc aggttacttt tcagctgttt aaaagcttta    180
```

```
gaagagtcag aataaatttc agcaaacctg aagcggcagc aagagcgcga atagaactcc    240
acgaaacaga cttcaatggg cagaagctaa agctatattt tgcacaggtg cagatgtccg    300
gcgaagtgcg ggacaagtcc tatctcctgc cgccccagcc tgtcaagcag ttcctcatct    360
cccctccagc ctctcccccg gtggggtgga agcagagcga agatgcgatg cctgttataa    420
attatgattt actctgtgct gtttccaaat tgggaccagg agagaaatat gaacttcacg    480
cgggaacaga gtcgacaccc agcgtggtgg ttcatgtctg tgaaagtgaa actgaagagg    540
aagaagagac aaaaaacccc aaacagaaaa ttgcccagac gaggcgcccc gaccctccga    600
ccgcagcgtt gaatgagccc cagacctttg attgcgcgct gtgaggccct tggttgtggt    660
gcgaggcggc tgcctggtg ggctctggcc atggcgctct gtgcctgcgg ccgatgcgtt    720
gctgcgaaca gcataggtga gactctgccg agtgaggtat aggtcttctc accacgcctg    780
tactgcagac acggtcgtgt agagtagcag ctgatttgac ctgtcccaga ttttaagtga    840
tattccaaaa gggactttac attaaaggag aagcccccaa gatgtggcca cccttaacca    900
tttttaaata gtaacaaatt aggaaaacag ctcccctccc ctccagccat gtaagtcctc    960
ctgattctgt atcacatgag acaccaaaaa ctggaaatgt agtcacaccc agtacagtac   1020 cattttatg aatttaaaaa tagtcttata attttaattg tttgtgggta tttttctact   1080
ggtataaata gcttctaatt aataaatcga tcaaaggttg ttactcagta tacatgaaat   1140
tttttgcagg aaaagaaacc agaaatacag aataattcat agaaatcatg gttctcaagt   1200
atttgttcaa ttagctttgg ggaagaaatg ccaaatccac tttgaggatg agtcttacga   1260
cacagatcca cccacatgtt gctcttatct ggaatttggg acaaagcaat gcacaggccc   1320
tcattcctga tgtggcgccc tccagacatg gctgcccagg aaggacggcc actttagaag   1380
tgggacgtat caccagtaag cttgaatgat taggatcgga ggtggctact gcattctgcc   1440
gttcgtgacc gtgttctagc ctgtagacca cccagctacc ttcattcacc agtttttatc   1500
cttcaccttt tccagtatct tgttaaccac tagttcttga gttttttggc tatgatgtgt   1560
acgtttatgt atgtcattca tggactttca actagaaaag gtaatgataa ggttttctga   1620
agaccatttg taaattgtcc atttaaccat ttttcagctt gctttgaaac aaaagtcaca   1680
cctactattt ttctatgaat tagggaatga gggggagatc attcagtttt acttttctttt  1740 ttgttgaaat tttgtacccg gattgcagtt ggcacttttc ctaaaacaga attgtttccc   1800
acttaggtgt cagaatgtac ctttgaactt ccctaagaag cagcaggatc tttttaactc   1860
tctctggtct gtttagactt tgaagtccct tctgtagaaa agtctcataa ctgagaaggc   1920
tctgttttgg gccgggtggg tctgctggcc tccactcact gtgctgtttc ctttgagtgg   1980
cacacttggg aagctccggg gcatgtgaag gagctgcaaa catgagaact aatgaaccaa   2040
ggcggctgcc accaggaagg aacagaacgc aggcattcaa ccatgacgtc tgcacagtgt   2100
tagtaacatg tcattgtggt ttcgttctca ctgtggtaaa atttatttct gagcacttaa   2160
actgtgttgc ataccctaa tttttttttt ttctgtatct tccttgccct caaataccct    2220
gaggtgataa actgttccag ttgtagccaa ctaccactgc taggcctcaa tgtaaattca   2280
gttgaaattt gcaattctat cagcaattta atgtattgaa ttcagatcat catttgtcat   2340
tttaaccgac aaccacccaa taaatttact ctgcagttct gaactcaaaa aa           2392
```

<210> SEQ ID NO 22
<211> LENGTH: 2187
<212> TYPE: DNA

<213> ORGANISM: Homo Sapiens

<400> SEQUENCE: 22

```
tgggtgcctg atagacatcc taggactata cagaaggaaa aggcccactt tgggggataa      60
tgctgaggga cactatgaaa tcttggaatg atagccagtc agatctgtgt agcactgacc     120
aagaagagga agaagagatg attttggtg aaaatgaaga tgatttggat gagatgatgg     180
atttaagtga tctgcctacc tcactttttg cttgcagcgt ccatgaagca gtgtttgagg     240
cacgagagca gaaggagaga aatatgaact tcacgcggga acagagtcga cacccagcgt     300
ggtggttcat gtctgtgaaa gtgaaactga agaggaagaa gagacaaaaa acccccaaaca     360
gaaaattgcc cagacgaggc gccccgaccc tccgaccgca gcgttgaatg agccccagac     420
ctttgattgc gcgctgtgag gcccttggtt gtggtgcgag gcggctgccc tggtgggctc     480
tggccatggc gctctgtgcc tgcggccgat gcgttgctgc aacagcata ggtgagactc     540
tgccgagtga ggtataggtc ttctcaccac gcctgtactg cagacacggt cgtgtagagt     600
agcagctgat ttgacctgtc ccagatttta agtgatattc caaagggac tttacattaa     660
aggagaagcc cccaagatgt ggccacccct aaccattttt aaatagtaac aaattaggaa     720
aacagctccc ctcccctcca gccatgtaag tcctcctgat tctgtatcac atgagacacc     780
aaaaactgga aatgtagtca cacccagtac agtaccattt ttatgaattt aaaaatagtc     840
ttataattt aattgtttgt gggtattttt ctactggtat aaatagcttc taattaataa     900
atcgatcaaa ggttgttact cagtatacat gaattttttt gcaggaaaag aaaccagaaa     960
tacagaataa ttcatagaaa tcatggttct caagtatttg ttcaattagc tttggggaag    1020
aaatgccaaa tccactttga ggatgagtct tacgacacag atccacccac atgttgctct    1080
tatctggaat ttgggacaaa gcaatgcaca ggccctcatt cctgatgtgg cgccctccag    1140
acatggctgc ccaggaagga cggccacttt agaagtggga cgtatcacca gtaagcttga    1200
atgattagga tcgcaggtgg ctactgcatt ctgccgttcg tgaccgtgtt ctagcctgta    1260
gaccacccag ctaccttcat tcaccagttt ttatccttca ccttttccag tatcttgtta    1320
accactagtt cttgagtttt ttggctatga tgtgtacgtt tatgtatgtc attcatggac    1380
tttcaactag aaaaggtaat gataaggttt tctgaagacc atttgtaaat tgtccattta    1440
accattttc agcttgcttt gaaacaaaag tcacacctac tattttttcta tgaattaggg    1500
aatgagggg agatcattca gttttacttt tcttttttgtt gaaattttgt acccggattg    1560
cagttggcac ttttcctaaa acagaattgt ttcccactta ggtgtcagaa tgtacctttg    1620
aacttcccta agaagcagca ggatcttttt aactctctct ggtctgttta gactttgaag    1680
tcccttctgt agaaaagtct cataactgag aaggctctgt tttgggccgg gtgggtctgc    1740
tggcctccac tcactgtgct gtttcctttg agtggcacac ttgggaagct ccggggcatg    1800
tgaaggagct gcaaacatga gaactaatga accaaggcgg ctgccaccag gaaggaacag    1860
aacgcaggca ttcaaccatg acgtctgcac agtgttagta acatgtcatt gtggtttcgt    1920
tctcactgtg gtaaaattta tttctgagca cttaaactgt gttgcatacc cctaattttt    1980
tttttttctg tatcttcctt gccctcaaat accctgaggt gataaactgt tccagttgta    2040
gccaactacc actgctaggc ctcaatgtaa attcagttga aatttgcaat tctatcagca    2100
atttaatgta ttgaattcag atcatcattt gtcatttttaa ccgacaacca cccaataaat    2160
ttactctgca gttctgaact caaaaaa                                         2187
```

<210> SEQ ID NO 23
<211> LENGTH: 1955
<212> TYPE: DNA
<213> ORGANISM: Homo Sapiens

<400> SEQUENCE: 23

```
caggcactaa gctgggcact gggaatgtaa taaaatagtc aaggtcccac cttctaagac    60
tgtccgacag ggaaacgaac aagagtcaaa taaggcagaa gatgtgatgt aatacaccta   120
cgaaatctca gagggttgta gggtcgtggg agctcaagtg agacacttaa cctggcctga   180
gacattccag aaggcctcct gaagaactga catctgaact gagaactgaa ggaagatgag   240
tactagtgag gctaccggac gtgaatgtgg agattgtgca gggcaatgca agaggaggct   300
gtagaagtca acctggctag atcacagcgg ggtgtatgtg gggcaggagc ttctttgttt   360
gaatttgctc ctgagaggat gaggcctcct agagcactgg ctcctggaca gcaacctcct   420
ttggtgcctt gtgaccaggg ccctgatggt tcattagatg gagccttcga gtcttaggga   480
gttgccgcag ggtccccaca gcggctcccg acggttgtga accagcatcc atcctccacg   540
gattccggca acccgcctgg ccctggacgt gtctcaactg gcccgcgtga ggggccgccc   600
cggaaatgac gcgctgcccc gctggccaag cggaagtgga gatggcggag ctgtacgtga   660
agccgggcaa caaggaacgc ggctggaacg acccgccgca gttctcatac gggctgcaga   720
cccaggccgg cggacccagg cgctcgctgc ttaccaagag ggtcgccgca ccccaggatg   780
gatcccccag agtccccgca tcagagactt ctcctgggcc tccccaatg gggcctccac    840
ctccttcaag taaggctccc aggtccccac ctgtggggag tggtcctgcc tctggcgtgg   900
agcccacaag tttcccagtc gagtctgagg ctgtgatgga ggatgtgctg agacctttgg   960
aacaggcatt ggaagactgc cgtggccaca caaggaagca ggtatgtgat gacatcagcc  1020
gacgcctggc actgctgcag gaacagtggg ctggaggaaa gttgtcaata cctgtaaaga  1080
agagaatggc tctactggtg caagagcttt caagccaccg gtgggacgca gcagatgaca  1140
tccaccgctc cctcatggtt gaccatgtga ctgaggtcag tcagtggatg gtaggagtta  1200
aaagattaat tgcagaaaag aggagtctgt tttcagagga ggcagccaat gaagagaaat  1260
ctgcagccac agctgagaag aaccatacca taccaggctt ccagcaggct tcataatcct  1320
cggttcccca gactcaccgg acaccatctc ctatgccttg gagaccttct gtcacttggc  1380
tcccttctta ccaccaccaa gactgtccca ctgggcctga cccacctatg agggaagaag  1440
tcccacctgg gccagaggga gttcatgtgt tactcataac atgcatttca ataaaaacat  1500
ctctgcggtg ggccttgggt aggagagatg aacccttccg gtgccaagct agtccctct   1560
ggtgtcctcg actgccctgc tccctgtgta tctgcaaacc tctgttctcc cttctccatt  1620
catcaggaag ggatctgctg ggtaaagtca gactactgcc taccactttt tcccaaagta  1680
gactgaaagc acatcctgtg ctgggcggag cagctgtgtt tggatggttt catttcagca  1740
tgagaacaga ctcaaataga acggggagac tttcccctca acaaaaggaa agacagtcct  1800
atttgcactg tatcaccctt gagatactac tgttacagag attagaacca cattgagtgg  1860
ggttttctgt gtaaatcgaa ggagaaaaag accagattac tgagattggg gattgtaact  1920
ctgacttgcc aaacaaactg ctgcctcata aaaaa                             1955
```

<210> SEQ ID NO 24
<211> LENGTH: 1270
<212> TYPE: DNA
<213> ORGANISM: Homo Sapiens

<400> SEQUENCE: 24

```
ggagatggcg gagctgtacg tgaagccggg tgagcgcagc cggcgggcta gggcactagg      60
ttgtcgcccc ggcctaggct gggggcggtt gcggcgctta gtatggaccc tctgtctccc     120
ccagccccag tataagctaa cagtggagtt ccgggctcgc ttcacacatc cctcgcctcc     180
gcaggcaaca aggaacgcgg ctggaacgac ccgccgcagt tctcatacgg gctgcagacc     240
caggccggcg gacccaggcg ctcgctgctt accaagaggg tcgccgcacc ccaggatgga     300
tcccccagag aagcaggtat gtgatgacat cagccgacgc ctggcactgc tgcaggaaca     360
gtgggctgga ggaaagttgt caatacctgt aaagaagaga atggctctac tggtgcaaga     420
gctttcaagc caccggtggg acgcagcaga tgacatccac cgctccctca tggttgacca     480
tgtgactgag gtcagtcagt ggatggtagg agttaaaaga ttaattgcag aaaagaggag     540
tctgttttca gaggaggcag ccaatgaaga gaaatctgca gccacagctg agaagaacca     600
taccatacca ggcttccagc aggcttcata atcctcggtt ccccagactc accggacacc     660
atctcctatg ccttggagac cttctgtcac ttggctccct tcttaccacc accaagactg     720
tcccactggg cctgacccac ctatgaggga agaagtccca cctgggccag agggagttca     780
tgtgttactc ataacatgca tttcaataaa aacatctctg cggtgggcct tgggtaggag     840
agatgaaccc ttccggtgcc aagctagtcc cctctggtgt cctcgactgc cctgctccct     900
gtgtatctgc aaacctctgt tctcccttct ccattcatca ggaagggatc tgctgggtaa     960
agtcagacta ctgcctacca cttttttccca agtagactg aaagcacatc ctgtgctggg    1020
cggagcagct gtgtttggat ggtttcattt cagcatgaga acagactcaa atagaacggg    1080
gagacttttc cctcaacaaa aggaaagaca gtcctatttg cactgtatca cccttgagat    1140
actactgtta cagagattag aaccacattg agtggggttt tctgtgtaaa tcgaaggaga    1200
aaaagaccag attactgaga ttggggattg taactctgac ttgccaaaca aactgctgcc    1260
tcataaaaaa                                                             1270
```

<210> SEQ ID NO 25
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 25

```
atagccacct ccttgtta                                                     18
```

<210> SEQ ID NO 26
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 26

```
taatcgagtc cagagtcat                                                    19
```

<210> SEQ ID NO 27
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 27
tagaacgtgt acgcagag                                               18

<210> SEQ ID NO 28
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 28
caatggtgtg gtagatcc                                               18

<210> SEQ ID NO 29
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 29
ggttcagaag accatagc                                               18

<210> SEQ ID NO 30
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 30
atcttatcgc atccactc                                               18

<210> SEQ ID NO 31
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 31
accaggaagg aacagaac                                               18

<210> SEQ ID NO 32
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 32
agaacgaaac cacaatgac                                              19

<210> SEQ ID NO 33
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 33
gcagccaatg aagagaaa                                               18

<210> SEQ ID NO 34
<211> LENGTH: 18
<212> TYPE: DNA

<213> ORGANISM: Artificial Sequence
<220> FEATURE:
<223> OTHER INFORMATION: Synthetic oligonucleotide

<400> SEQUENCE: 34
gggaaccgag gattatga                                                18

<210> SEQ ID NO 35
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 35
gccgcagtga tgttctagc                                               19

<210> SEQ ID NO 36
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 36
tctgctgccg tgcaaatc                                                18

<210> SEQ ID NO 37
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 37
cgatgctacc acctaatagt                                              20

<210> SEQ ID NO 38
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 38
taggctggac agaagagt                                                18

<210> SEQ ID NO 39
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 39
acctgtcgtt attcctatat cc                                           22

<210> SEQ ID NO 40
<211> LENGTH: 18
<212> TYPE: DNA
<213> ORGANISM: Artificial Sequence

```
<220> FEATURE:
<223> OTHER INFORMATION: Synthetic oligonucleotide

<400> SEQUENCE: 40
gaaaccgtgt tccctgtg                                                   18
```

KIT FOR THE PROGNOSIS OF COLORECTAL CANCER

TECHNICAL FIELD

The present invention relates to a kit, and especially to a kit for the prognosis of colorectal cancer.

TECHNICAL BACKGROUND

Colorectal cancer is one of the commonest malignant tumors, which ranks fifth and fourth in tumor incidence in US and China, respectively, and is the third cause of death for cancer patients in Europe. Blood and lymph node metastases of colorectal cancer seriously affect the prognosis of colorectal cancer, and they are important causes for the death of patients. The incidence of colorectal cancer is increasing at a rate of 2% worldwide every year. Thus, there is a need for means which can effectively prognose the development and outcome of colorectal cancer.

SUMMARY OF THE INVENTION

In order to solve the above problem, the present invention provides a kit for the prognosis of colorectal cancer.

The present invention provides a kit for the prognosis of colorectal cancer, characterized in that it comprises reagents for detecting the expression level of any one or more genes selected from the following five genes: BST1, as shown in SEQ ID NO:1; MGST1, as shown in SEQ ID NO: 2, 3, 4, 5, 6, 7, 8, 9 or 10; HP, as shown in SEQ ID NO: 11 or 12; RCAN3, as shown in SEQ ID NO: 13, 14, 15, 16, 17, 18, 19, 20, 21 or 22; and SRA1, as shown in SEQ ID NO: 23 or 24.

In one embodiment, the reagents are reagents for detecting the amount of RNA, especially the amount of mRNA, transcribed from the gene.

In one embodiment, the reagents are reagents for detecting the amount of cDNA complementary to the mRNA.

In one embodiment, the reagents are reagents for detecting the amount of cRNA complementary to the cDNA.

In one embodiment, the reagents comprise a probe.

In one embodiment, the reagents are reagents for detecting the amount of polypeptide encoded by the gene.

In one embodiment, the reagents comprise an antibody, an antibody fragment, or an affinity protein.

Also provided is use of the reagents for detecting the expression level of any one or more genes in the preparation of a kit for the prognosis of colorectal cancer, wherein said one or more genes are selected from the following five genes: BST1, as shown in SEQ ID NO: 1; MGST1, as shown in SEQ ID NO: 2, 3, 4, 5, 6, 7, 8, 9 or 10; HP, as shown in SEQ ID NO: 11 or 12; RCAN3, as shown in SEQ ID NO: 13, 14, 15, 16, 17, 18, 19, 20, 21 or 22; and SRA1, as shown in SEQ ID NO: 23 or 24.

In one embodiment, the reagents are reagents for detecting the amount of RNA, especially the amount of mRNA, transcribed from the gene.

In one embodiment, the reagents are reagents for detecting the amount of cDNA complementary to the mRNA.

In one embodiment, the reagents are reagents for detecting the amount of cRNA complementary to the cDNA.

In one embodiment, the reagents comprise a probe.

In one embodiment, the reagents are reagents for detecting the amount of polypeptide encoded by the gene.

In one embodiment, the reagents comprise an antibody or an affinity protein.

The present invention provides a method for detecting gene expression in a human sample, especially human blood sample, comprising: (1) determining the level of RNA transcribed from any one or more genes in a blood sample of a subject selected from the following group of genes: BST1, as shown in SEQ ID NO: 1; MGST1, as shown in SEQ ID NO: 2, 3, 4, 5, 6, 7, 8, 9 or 10; HP, as shown in SEQ ID NO: 11 or 12; RCAN3, as shown in SEQ ID NO: 13, 14, 15, 16, 17, 18, 19, 20, 21 or 22; and SRA1, as shown in SEQ ID NO: 23 or 24; and (2) detecting the gene expression in the blood sample of the subject.

Preferably, in the step (1) the levels of RNAs transcribed from the five genes in the group are determined.

In one embodiment, the sample is a blood sample of a patient suffering from colorectal cancer.

In one embodiment, at least one oligonucleotide is used in the step (1).

In one embodiment, one oligonucleotide only hybridizes with RNA transcribed from one gene, and/or can hybridize with cDNA complementary to the RNA transcribed from the gene.

In one embodiment, said step (1) comprises the following steps: (a) amplifying RNA transcribed from the gene, so as to obtain an amplified product; (b) detecting the amount of the amplified product obtained in step (a) by using at least one primer.

In one embodiment, said step (1) comprises the following steps: (i) using at least one probe to hybridize with cDNA which is complementary to the RNA transcribed from the gene, so as to obtain a hybridization product; (ii) detecting the amount of the hybridization product obtained in step (i).

In one embodiment, the step (1) comprises a process for amplifying the RNA transcribed from the gene.

In one embodiment, the step (1) comprises a process for detecting the amount of cDNA which is complementary to the RNA transcribed from the gene.

In one embodiment, at least one probe is used in the step (1).

In one embodiment, at least one primer is used in the step (1).

The present invention provides an oligonucleotide, which only hybridizes with RNA transcribed from one gene, and/or, which can hybridize with cDNA complementary to the RNA transcribed from the gene selected from a group consisting of BST1, as shown in SEQ ID NO: 1; MGST1, as shown in SEQ ID NO: 2, 3, 4, 5, 6, 7, 8, 9 or 10; HP, as shown in SEQ ID NO: 11 or 12; RCAN3, as shown in SEQ ID NO: 13, 14, 15, 16, 17, 18, 19, 20, 21 or 22; and SRA1, as shown in SEQ ID NO: 23 or 24.

The oligonucleotide is selected from the nucleotide sequences as shown in SEQ ID NOs: 25-34.

The present invention provides a kit for detecting gene expression in a human sample, especially a human blood sample, characterized in that it comprises specific partners corresponding to the five expression products of the following five genes: BST1, as shown in SEQ ID NO: 1; MGST1, as shown in SEQ ID NO: 2, 3, 4, 5, 6, 7, 8, 9 or 10; HP, as shown in SEQ ID NO: 11 or 12; RCAN3, as shown in SEQ ID NO: 13, 14, 15, 16, 17, 18, 19, 20, 21 or 22; and SRA1, as shown in SEQ ID NO: 23 or 24, and each partner specifically binds to one gene, respectively.

In one embodiment, the specific partners comprise an oligonucleotide, especially a probe and/or a primer.

In one embodiment, the specific partners are selected from a set of nucleotide sequences as shown in SEQ ID NOs: 25-34.

In one embodiment, the specific partners include an antibody and/or an affinity protein.

The present invention provides a method for prognosis of development situation of a patient suffering from colorectal cancer by detecting a blood sample, characterized in that it comprises the following steps: a) obtaining a blood sample, and detecting the amount of expression product of any one or more genes selected from the following five genes: BST1, as shown in SEQ ID NO: 1; MGST1, as shown in SEQ ID NO: 2, 3, 4, 5, 6, 7, 8, 9 or 10; HP, as shown in SEQ ID NO: 11 or 12; RCAN3, as shown in SEQ ID NO: 13, 14, 15, 16, 17, 18, 19, 20, 21 or 22; and SRA1, as shown in SEQ ID NO: 23 or 24; b) inputting the amount of the expression product of the gene detected in the step a) into a support vector machine model, and calculating a prognosis index; and c) evaluating the prognosis of the patient suffering from colorectal cancer based on the result obtained in step b).

If the prognosis index of a sample is more than 0, it will be categorized as a case with high risk; and if the prognosis index of a sample is less than 0, it will be categorized as a case with low risk. Preferably, in the step a) the amount of expression product of each gene in the five genes is detected.

In one embodiment, in the step a), the amount of expression product of at least one gene is detected by contacting the expression product of said gene with the specific partner of the expression product.

In one embodiment, in step a) for detecting the amount of expression product of a gene, the nucleotide sequences of the genes are selected from a set of sequences as shown in SEQ ID NOs: 1-24.

In one embodiment, the expression product in step a) comprises at least one RNA transcript or one polypeptide.

In one embodiment, the expression product comprises at least one mRNA.

In one embodiment, the RNA transcript is detected and quantified by hybridization, amplification or sequencing.

In one embodiment, the RNA transcript is brought into contact with at least one probe and/or at least one primer under a preset condition allowing hybridization of the probe and/or primer with the RNA transcript.

In one embodiment, the cDNA of the RNA transcript is brought into contact with at least one probe and/or at least one primer under the preset condition allowing hybridization of the probe and/or primer with the cDNA.

In one embodiment, the detection of the polypeptide is implemented by contacting the polypeptide with at least one specific ligand, especially an antibody or an affinity protein.

In one embodiment, the polypeptide is brought into contact with at least two specific ligands, especially two antibodies, two affinity proteins, or one antibody and one affinity protein.

The present invention provides a kit for in vitro screening of the risk of having human colorectal cancer, which comprises a specific partner corresponding to the expression product of any one or more genes of the following five genes: BST1, as shown in SEQ ID NO: 1; MGST1, as shown in SEQ ID NO: 2, 3, 4, 5, 6, 7, 8, 9 or 10; HP, as shown in SEQ ID NO: 11 or 12; RCAN3, as shown in SEQ ID NO: 13, 14, 15, 16, 17, 18, 19, 20, 21 or 22; and SRA1, as shown in SEQ ID NO: 23 or 24, and each partner specifically binds to one gene, respectively;

the specific partner specifically binds to the expression product of the gene; and the nucleic acid sequences of the five genes are selected from the set of the sequences as shown in SEQ ID NOs: 1-24.

Preferably, the kit comprises the specific partner corresponding to the expression product of any gene of the five genes.

In one embodiment, the specific partner comprises at least one hybridization probe.

In one embodiment, the specific partner comprises at least one hybridization probe and at least one primer.

In one embodiment, the specific partner comprises at least one hybridization probe and two primers.

In one embodiment, the specific partner comprises at least one specific ligand, especially an antibody or an affinity protein.

In one embodiment, the specific partner comprises at least two specific ligands, especially two antibodies, two affinity proteins, or one antibody and one affinity protein.

Also provided is use of a specific partner corresponding to the expression product of any one or more genes of the five genes with nucleotide sequences as shown in SEQ ID NOs: 1-24 in the preparation of reagents for in vitro screening of the risk of suffering from colorectal cancer, and the specific partner specifically binds to the expression products of the five genes.

Preferably, the specific partner is the specific partner corresponding to the expression product of any one gene of the five genes.

In one embodiment, the specific partner comprises at least one hybridization probe.

In one embodiment, the specific partner comprises at least one hybridization probe and at least one primer.

In one embodiment, the specific partner comprises at least one hybridization probe and two primers.

In one embodiment, the specific partner comprises at least one specific ligand, especially an antibody or an affinity protein.

In one embodiment, the specific partner comprises at least two specific ligands, especially two antibodies, two affinity proteins, or one antibody and one affinity protein.

The detection of gene expression level in the present invention can be implemented by detecting the RNA transcript.

The term "RNA transcript" refers to total RNA, i.e. coding or non-coding RNA, which includes RNAs directly originated from peripheral blood samples, and which also includes RNAs indirectly originated from blood samples after cell disruption. Method for cell disruption can be adopted from the magnetic and mechanical disruption methods as disclosed in Patent Application WO 99/05338, or can be adopted from the magnetic disruption methods as disclosed in Patent Application WO 99/53340, or can be adopted from the mechanical disruption methods as disclosed in Patent Application WO 99/15321. Methods known in the art, of course, can also be adopted, such as thermal disruption, hyperosmotic disruption, or chemical disruption methods using a disruption liquid like guanidine salt etc. After cell disruption, the nucleic acids need to be isolated from other cell components produced in the disruption step. Generally, centrifugation can be used to purify nucleic acids. Total RNA includes tRNA, mRNA, and rRNA, wherein the mRNA includes mRNAs transcribed from a target gene, and also includes mRNAs from other non-target genes.

In the present invention, RNA transcript can be detected and quantified by hybridization, amplification, or sequencing methods, e.g., by hybridizing an RNA transcript with a probe or a primer.

The term "hybridization" is intended to mean the process during which, under appropriate conditions, two nucleotide fragments bind with stable and specific hydrogen bonds so as to form a double-stranded complex. These hydrogen bonds form between the complementary adenine (A) and thymine (T) (or uracile (U)) bases (this is referred to as an A-T bond) or between the complementary guanine (G) and cytosine (C) bases (this is referred to as a G-C bond).

The hybridization of two nucleotide fragments may be complete (reference is then made to complementary nucleotide fragments or sequences), i.e. the double-stranded complex obtained during this hybridization comprises only A-T bonds and C-G bonds. This hybridization may be partial (reference is then made to sufficiently complementary nucleotide fragments or sequences), i.e. the double-stranded complex obtained comprises A-T bonds and C-G bonds that make it possible to form the double-stranded complex, but also bases not bound to a complementary base.

The hybridization between two nucleotide fragments depends on the working conditions that are used, and in particular on the stringency. The stringency is defined in particular as a function of the base composition of the two nucleotide fragments, and also by the degree of mismatching between two nucleotide fragments. The stringency can also depend on the reaction parameters, such as the concentration and the type of ionic species present in the hybridization solution, the nature and the concentration of denaturing agents and/or the hybridization temperature. All these data are well known and the appropriate conditions can be determined by those skilled in the art. In general, depending on the length of the nucleotide fragments that it is intended to hybridize, the hybridization temperature is between approximately 20 and 70° C., in particular between 35 and 65° C. in a saline solution at a concentration of approximately 0.5 to 1 M.

The term "amplification primer" is intended to mean a nucleotide fragment comprising from 5 to 100 nucleotides, preferably from 15 to 30 nucleotides that allow the initiation of an enzymatic polymerization, for instance an enzymatic amplification reaction.

The term "enzymatic amplification reaction" is intended to mean a process which generates multiple copies of a nucleotide fragment through the action of at least one enzyme. Such amplification reactions are well known to those skilled in the art and mention may in particular be made of the following techniques: PCR (polymerase chain reaction), as described in U.S. Pat. No. 4,683,195, U.S. Pat. No. 4,683,202 and U.S. Pat. No. 4,800,159, LCR (ligase chain reaction), disclosed for example, in patent application EP 0 201 184, RCR (repair chain reaction), described in patent application WO 90/01069, 3SR (self sustained sequence replication) with patent application WO 90/06995, NASBA (nucleic acid sequence-based amplification) with patent application WO 91/02818, TMA (transcription mediated amplification) with U.S. Pat. No. 5,399,491.

When the enzymatic amplification is a PCR, the specific reagent comprises at least two amplification primers, specific for a target gene, that allow the amplification of the material specific for the target gene. The material specific for the target gene then preferably comprises a complementary DNA obtained by reverse transcription of mRNA derived from the target gene (cDNA) or a complementary RNA obtained by transcription of the cDNAs specific for a target gene (cRNA). When the enzymatic amplification is a PCR carried out after a reverse transcription reaction, reference is made to RT-PCR.

The term "hybridization probe" is intended to mean a nucleotide fragment comprising at least 5 nucleotides, such as from 5 to 100 nucleotides, having a hybridization specificity under given conditions so as to form a hybridization complex with the expression product specific for a target gene (or amplified product of said expression product). In the present invention, the expression product of a target gene includes mRNA of the target gene, and the amplified product of the target expression product includes cDNA complementary to the target product mRNA, or cRNA complementary to the cDNA. The hybridization probe may include a label for its detection.

The term "detection" is intended to mean either a direct detection such as a counting method, or an indirect detection by a method of detection using a label. Many methods of detection exist for detecting nucleic acids (see, for example, Kricka et al., Clinical Chemistry, 1999, no 45 (4), p. 453-458 or Keller G H. et al., DNA Probes, 2nd Ed., Stockton Press, 1993, sections 5 and 6, p. 173-249).

The term "label" is intended to mean a tracer capable of generating a signal that can be detected. A non limiting list of these tracers includes enzymes which produce a signal that can be detected, for example, by colorimetry, fluorescence or luminescence, such as horseradish peroxidase, alkaline phosphatase, β-galactosidase, glucose-6-phosphate dehydrogenase; chromophores such as fluorescent, luminescent or dye compounds; electron dense groups detectable by electron microscopy or by virtue of their electrical properties such as conductivity, by amperometry or voltametry methods, or by impedance measurement; groups that can be detected by optical methods such as diffraction, surface plasmon resonance, or contact angle variation, or by physical methods such as atomic force spectroscopy, tunnel effect, etc.; radioactive molecules such as $^{32}P$, $^{35}S$, or $^{125}I$.

The hybridization probe may be a "detection" probe. In this case, the "detection" probe is labeled by means of a label, such as a "molecular beacon" detection probe as described by Tyagi & Kramer (Nature biotech, 1996, 14:303-308). The "molecular beacon" has a stem-loop-type structure and contains a fluorophore and a "quencher" group. The binding of the specific loop sequence with its complementary target nucleic acid sequence causes the stem to unroll and the emission of a fluorescence during excitation at the appropriate wavelength. The detection probe in particular may be a "Reporter Probe", comprising a "color-coded barecode" according to NanoString™'s technology.

The detection probe includes a fluorophore and a quenching agent, e.g., 6-carboxyl-fluorescein or 6-carboxyl-X-rhodamine, and there is quenching agent at 3'-end: 4-Dimethylaminoazobenzene sulfonyl chloride.

For the detection of the hybridization reaction, target sequences have to be labeled, directly (in particular by the incorporation of a label within the target sequence) or indirectly (in particular using a detection probe as defined above). It is in particular possible to carry out, before the hybridization step, a step comprising labeling and/or cleaving the target sequence, for example using a labeled deoxyribonucleotide triphosphate during the enzymatic amplification reaction. The cleavage may be carried out in particular by the action of imidazole or of manganese chloride. The target sequence may also be labeled after the amplification step, for example by hybridizing a detection probe according to the sandwich hybridization technique described in document WO 91/19812. Another specific preferred method of labeling nucleic acids is described in application FR 2780059.

The hybridization probe may also be a "capture" probe. In this case, the "capture" probe can be immobilized on a solid substrate by any appropriate means, i.e. directly or indirectly, for example by covalence or adsorption. Solid substrate may be made of synthetic materials or natural materials, optionally chemically modified, in particular polysaccharides such as cellulose-based materials, for example paper, cellulose derivatives such as cellulose acetate and nitrocellulose or dextran, polymers, copolymers, in particular based on styrene-type monomers, natural fibers such as cotton, and synthetic fibers such as nylon; inorganic materials such as silica, quartz, glasses or ceramics; latices; magnetic particles; metal derivatives, gels, etc. The solid substrate may be in the form of a microtitration plate, of a membrane as described in application WO-A-94/12670 or of a particle. It is also possible to immobilize on the substrate several different capture probes, each being specific for a target gene. In particular, a biochip on which a large number of probes can be immobilized may be used as substrate. The term "biochip" is intended to mean a solid substrate that is small in size, to which a multitude of capture probes are attached at predetermined positions.

The biochip, or DNA chip, concept dates from the beginning of the 1990s. It is based on a multidisciplinary technology that integrates microelectronics, nucleic acid chemistry, image analysis and information technology. The operating principle is based on a foundation of molecular biology: the hybridization phenomenon, i.e. the pairing, by complementarity, of the bases of two DNA and/or RNA sequences. The biochip method is based on the use of capture probes attached to a solid substrate, on which probes a sample of target nucleotide fragments directly or indirectly labeled with fluorochromes is made to act. The capture probes are positioned specifically on the substrate or chip and each hybridization gives a specific piece of information, in relation to the target nucleotide fragment. The pieces of information obtained are cumulative, and make it possible to quantify the level of expression of one or more target genes. In order to analyze the expression of a target gene, a substrate comprising a multitude of probes, which correspond to all or part of the target gene, which is transcribed to mRNA, can then be prepared. For the purpose of the present invention, the term "low-density substrate" is intended to mean a substrate comprising fewer than 50 probes, the term "medium-density substrate" is intended to mean a substrate comprising from 50 probes to 10 000 probes, and the term "high-density substrate" is intended to mean a substrate comprising more than 10 000 probes.

After hybridization of the cRNA or cDNA of the target gene and the specific capture probe, the substrate or chip is washed and the labeled cDNA or cRNA/capture probe complexes are revealed by means of a high-affinity ligand bound, for example, to a fluorochrome-type label. The analysis of the fluorescence is processed by information technology. By way of indication, mention may be made of the DNA chips developed by the company Affymetrix ("Accessing Genetic Information with High-Density DNA arrays", M. Chee et al., Science, 1996, 274, 610-614. "Light-generated oligonucleotide arrays for rapid DNA sequence analysis", A. Caviani Pease et al., Proc. Natl. Acad. Sci. USA, 1994, 91, 5022-5026), for molecular diagnoses. In this technology, the capture probes are generally small in size, around 25 nucleotides. Other examples of biochips are given in the publications by G Ramsay, Nature Biotechnology, 1998, No. 16, p. 40-44; F. Ginot, Human Mutation, 1997, No. 10, p. 1-10; J. Cheng et al, Molecular diagnosis, 1996, No. 1 (3), p. 183-200; T. Livache et al, Nucleic Acids Research, 1994, No. 22 (15), p. 2915-2921; J. Cheng et al, Nature Biotechnology, 1998, No. 16, p. 541-546 or in U.S. Pat. No. 4,981,783, U.S. Pat. No. 5,700,637, U.S. Pat. No. 5,445,934, U.S. Pat. No. 5,744,305 and U.S. Pat. No. 5,807,522 The main characteristic of the solid substrate should be to conserve the hybridization characteristics of the capture probes on the target nucleotide fragments while at the same time generating a minimum background noise for the method of detection.

Capture probes can be immobilized on a substrate by the following three steps:

1. Depositing pre-synthesized probes on a slide carrier. The attachment of the probes is carried out by direct transfer, by means of micropipettes or of microdots or by means of an inkjet device. This technique allows the attachment of probes having a size ranging from a few bases (5 to 10) up to relatively large sizes of 60 bases (printing) to a few hundred bases (microdeposition).

Printing is an adaptation of the method used by inkjet printers. It is based on the propulsion of very small spheres of fluid at a rate that may reach 4000 drops/second. Microdeposition comprises attaching long probes of a few tens to several hundred bases to the surface of a glass slide. These probes are generally extracted from databases and are in the form of amplified and purified products. This technique makes it possible to produce macroarrays that carry approximately ten thousand spots, called recognition zones, of DNA on a surface area of a little less than 4 cm². Nylon membranes, referred to as "macroarrays", which carry products that have been amplified, generally by PCR, with a diameter of 0.5 to 1 mm and the maximum density of which is 25 spots/cm², are used. This very flexible technique is used by many laboratories. In the present invention, the latter technique is considered to be included among biochips. A certain volume of sample can, however, be deposited at the bottom of a microtitration plate, in each well, as in the case in patent applications WO-A-00/71750 and FR 00/14896, or a certain number of drops that are separate from one another can be deposited at the bottom of one and the same Petri dish, according to another patent application, FR 00/14691.

2. The second technique for attaching the probes to the substrate or chip is called in situ synthesis. This technique results in the production of short probes directly at the surface of the chip. It is based on in situ oligonucleotide synthesis (see, in particular, patent applications WO 89/10977 and WO 90/03382) and is based on the oligonucleotide synthesizer process. It comprises moving a reaction chamber, in which the oligonucleotide extension reaction takes place, along the glass surface.

3. The third technique is called photolithography, which is a process that is responsible for the biochips developed by Affymetrix. It is also an in situ synthesis. Photolithography is derived from microprocessor techniques. The surface of the chip is modified by the attachment of photolabile chemical groups that can be light-activated. Once illuminated, these groups are capable of reacting with the 3' end of an oligonucleotide. By protecting this surface with masks of defined shapes, it is possible to selectively illuminate and therefore activate areas of the chip where it is desired to attach one or other of the four nucleotides. The successive use of different masks makes it possible to alternate cycles of protection/reaction and therefore to produce the oligonucleotide probes on spots of approximately a few tens of square micrometers. This resolution makes it possible to create up to several hundred thousand spots on a surface area of a few square centimeters. Photolithography has advantages: in bulk in parallel, it makes it possible to create a chip of N-mers in only 4 times cycles.

The following methods can also be used for hybridization detection of the expression of a target gene: (1) same as the above step (1), after having extracted, the total RNA from a biological sample as presented above, a reverse transcription step is carried out as described above in order to obtain the cDNAs of the mRNAs of the biological material. The polymerization of the complementary RNA of the cDNA is subsequently carried out using a T7 polymerase enzyme which functions under the control of a promoter and which makes it possible to obtain, from a DNA template, the complementary RNA. The mixtures including cRNAs specific for the target gene and the cRNAs specific for the non-target gene are then obtained. (2) All the cRNAs are brought into contact with a substrate on which are immobilized capture probes specific for the target gene, in order to carry out a hybridization reaction between the target-gene-specific cRNAs and the capture probes, the cRNAs not specific for the target gene not hybridizing to the capture probes. When it is desired to simultaneously analyze the expression of several target genes, several different capture probes can be immobilized on the substrate, each one being specific for a target gene. The hybridization reaction may also be preceded by a step comprising labeling and/or cleaving the target-gene-specific cRNAs as described above. (3) Detecting the results of the hybridization reactions. The detection can be carried out by bringing the substrate on which the capture probes specific for the target gene are hybridized with the target-gene-specific cRNA into contact with a "detection" probe labeled with a label, and detecting the signal emitted by the label. When the target-gene-specific cRNA has been labeled beforehand with a label, the signal emitted by the label is detected directly. The use of cRNA is particularly advantageous when a substrate of biochip type on which a large number of probes are hybridized is used.

The detection for the expression levels of genes in the invention can be accomplished by detecting polypeptides. Specifically, the polypeptides can be bound with at least one specific ligand. The above said reagent is reagent for detecting the amounts of polypeptides encoded by the genes.

Preferably, the reagents are antibodies, or affinity proteins. In preferred Examples of the invention, the expressed polypeptides are bound with at least two specific ligands. The specific ligand of the invention can be and antibody or an affinity protein called "Nanofitin™".

Said "antibody" includes polyclonal antibodies, monoclonal antibodies, humanized antibodies, and recombinant antibodies, and the preparation methods thereof are well known in the art.

Gene expression data are characterized in that they have large data size, high dimension, small sample size, and non-linearity. One of the important tasks for analyzing the gene expression data is to distinguish and categorize the samples, i.e. establishing a distinguishing model based on known gene expression data, and categorizing the unknown samples, which have important significance for the diagnosis of diseases. Traditional statistic categorizing methods such as linear distinguishing, and logistic distinguishing have great limitations, since these methods are essentially linear methods, and can hardly apply to complicated situations, furthermore, the number of variables (genes) in gene expression data analysis is much more than the case number of samples, and thus the calculation cannot be effectively conducted.

Support Vector Machine (SVM) is a novel machine learning method recently developed based on the principles of statistic learning. It adopts a principle of minimizing the structure risk, and can well solve the problem of small sample size learning, and the Support Vector Machine displays excellent performances, especially for gene expression data with high dimension, small sample size, and non-linearity. Guyon first applied the Support Vector Machine to the study of leukemia gene expression data, and accomplished a success (I. Guyon, Machine Learning, 2002, No. 46, p. 389-422; J.). Recently, investigators in China also demonstrated that the algorithm of the Support Vector Machine has advantageous performances (Z. Zhu, Journal of Clinical Oncology, 2009, No. 7, p. 1091-1099; Y. Xu, Clincial Cancer Research, 2013, No. 19, p. 3039-3045).

The kit of the invention can be used to effectively prognose the development situations of patients with colorectal cancer, and it can be readily operated with only blood examination, and thus the patients have good compliance, which provides reliable proofs for clinical treatments of colorectal cancer patients, with good application prospects.

Apparently, based on the above content of the invention, and according to common technical knowledge and conventional means, many other modifications, replacements and changes can be performed without departing from the above described basic technical idea of the invention.

Specific embodiment in the form of Examples below will be used to further illustrate the above contents of the invention. But it should not be construed that the scope of the above subjects will be limited to the following examples. Any technical solution, which is achieved base on the above contents of the invention, belongs to the scope of the invention.

DETAILED DESCRIPTION OF THE INVENTION

Example 1

Sample Collecting

Figure 1:
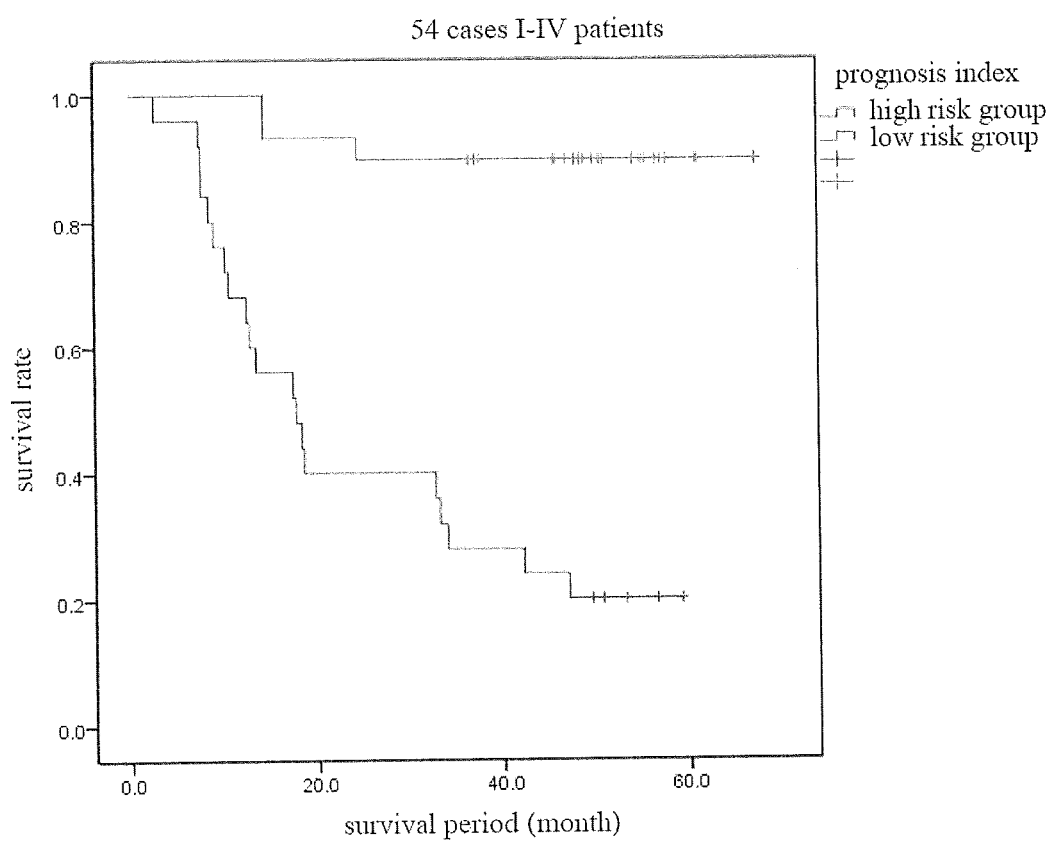
FIG. 1: Kaplan-Meier curve of the 54 cases of stage I-IV patients in group 1.

After informed consent, peripheral blood samples from 141 cases of colorectal cancer patients (CRCs) determined by clinical pathological diagnosis, were collected between October, 2006 and May, 2009.

The CRCs were recruited from Colorectal Surgical Department of Shanghai Cancer Center in Fudan University, and were all staged according to the TNM staging system suggested by the Union for International Cancer Control (UICC). None of the patients had received chemotherapy or radiotherapy before surgery operation. Patients having inherited colorectal cancer or inflammatory intestine diseases (Corhn's disease or ulcerative colitis) were excluded from the project. The population characteristics and clinical characteristics of the samples to be detected are shown in Table 1:

TABLE 1

Characteristics of the samples to be detected

| Variables | Group 1 | Group 2 |
| --- | --- | --- |
| Age | | |
| Average age | 58.1 | 54.7 |
| Range | 27-78 | 24-78 |

TABLE 1-continued

Characteristics of the samples to be detected

| Variables | Group 1 | Group 2 |
|---|---|---|
| Gender-Percentage (%) | | |
| Male | 31 (57.4) | 47 (54.0) |
| Female | 23 (42.6) | 40 (46.0) |
| Cancer location-Percentage (%) | | |
| colon | 22 (40.7) | 15 (17.2) |
| rectum | 32 (59.3) | 72 (82.8) |
| Staging-Percentage (%)* | | |
| Stage I | 18 (33.4) | — |
| Stage II | 8 (14.8) | 33 (37.9) |
| Stage III | 8 (14.8) | 54 (62.1) |
| Stage IV | 20 (37.0) | — |

Collection of blood samples: 2.5 ml peripheral blood taken from each participant was added into PAXgene™ blood RNA tube (PreAnalytix GmbH, Hombrechtikon, CH), and was treated in accordance to the manufacture's instructions. In Shanghai Cancer Center of Fudan University, China, blood samples of CRCs were collected one week after microscopical examination and before operation.

Staging: Group 1 contains 18 cases of stage I, 8 cases of stage II, 8 cases of stage III, and 20 cases of stage IV patients; group 2 contains 33 cases of stage II and 54 cases of stage III patients.

Example 2

Detection of Expression Amount for 5 Genes Including BST1 Etc.

1. Experiment Method (1) Selection of Housekeeping Gene

The geometrical mean of the expression levels of CSNK1G2, DECR1, and FARP1 were used as "housekeeping gene", and as the calibration factor for real-time quantitative PCR data.

(2) RNA Extraction and Real-Time Quantitative PCR Detection

Whole blood collection: 2.5 ml peripheral blood taken from each participant was added into PAXgene™ blood RNA tube (PreAnalytix GmbH, Hombrechtikon, CH), and was treated in accordance to the manufacture's instructions.

Total RNA extraction: according to the instructions, total RNA was extracted using PAXgene™ blood RNA system (PreAnalytix); the amount of total RNA was detected using spectrophotometer at OD value of 260 nm, the mass of total RNA was determined using RNA6000 Nano LabChipe kit on Agilent Bioanalyser (Agilent Technologies, Palo Alto, Calif., U.S.A.), and RNAs with an integrity number over 7.0 were used for analysis.

Reverse transcription: primers specific for the following target genes were used as primers, using QuantiTect® reverse transcription kit (Qiagen GmbH, Hilden, Germany), in accordance to the standard protocol, and 320 ng of the total RNA was used to conduct reverse transcription to obtain cDNA.

cDNA amplification: primers specific for the following target genes were used as primers, using SYBR Premix DimerEraser kit (Takara biotechnology, Dalian, China), in accordance to the standard protocol, and cDNA was amplified.

cDNA detection: Biosystems 7900HT Fast Real-Time PCR system (Life Technologies, Carlsbad, Calif., U.S.A.) was used for real time monitor of the amplification process, and based on the expression amount of the target gene and the expression amount of housekeeping gene, the relative expression amount of the target gene was calculated: $\Delta$Ct (relative expression amount of a gene)=Ct (target gene)−Ct (housekeeping gene), the relative expression amount of the target gene was calculated. A negative expression amount indicated that the Ct value of target gene is lower than the Ct value of the housekeeping gene; and a negative relative expression amount indicated that the Ct value of target gene is higher than the Ct value of the housekeeping gene.

Primer pairs for housekeeping genes:

1. CSNK1G2

F:5'-GCCGCAGTGATGTTCTAGC-3' (SEQ ID NO: 35)

R:3'-TCTGCTGCCGTGCAAATC-5' (SEQ ID NO: 36)

2. DECR1:

F:5'-CGATGCTACCACCTAATAGT-3' (SEQ ID NO: 37)

R:3'-TAGGCTGGACAGAAGAGT-5' (SEQ ID NO: 38)

3. FARP1:

F:5'-ACCTGTCGTTATTCCTATATCC-3' (SEQ ID NO: 39)

R:3'-GAAACCGTGTTCCCTGTG-5' (SEQ ID NO: 40)

Primer pairs for target genes:

1. BST1:

5'-ATAGCCACCTCCTTGTTA-3' (SEQ ID NO: 25)

R:3'-TAATCGAGTCCAGAGTCAT-5' (SEQ ID NO: 26)

2. MGST1:

5'-TAGAACGTGTACGCAGAG-3' (SEQ ID NO: 27)

R:3'-CAATGGTGTGGTAGATCC-5' (SEQ ID NO: 28)

3. HP:

F:5'-GGTTCAGAAGACCATAGC-3' (SEQ ID NO: 29)

3'-ATCTTATCGCATCCACTC-5' (SEQ ID NO: 30)

4. RCAN3:

F:5'-ACCAGGAAGGAACAGAAC-3' (SEQ ID NO: 31)

R:3'-AGAACGAAACCACAATGAC-5' (SEQ ID NO: 32)

5. SRA1:

F:5'-GCAGCCAATGAAGAGAAA-3' (SEQ ID NO: 33)

R:3'-GGGAACCGAGGATTATGA-5' (SEQ ID NO: 34)

Example 3

The Correlation Between Gene Expression Amount and Colorectal Cancer

1. The Correlation Between the Expression Amount of a Single Gene and the Prognosis of Colorectal Cancer According to the method of Example 2, the expression levels (the relative expression amounts) of 5 genes were respectively detected in the blood samples of the 54 patients in group 1 of Example 1, Cox Proportional Hazard Model analysis combined with forward feature selection algorithm was adopted to screen such target genes whose expression modes are significantly correlated to the prognosis of patients. Based on statistic analysis results, the expression modes of 5 genes had respective and significant predictive importance for the prognosis of patients.

(1) BST1 (Bone Marrow Stromal Cell Antigen 1)

| Gene symbol | Wald statistic | P value | risk ratio |
|---|---|---|---|
| BST1 | 5.6 | 0.02 | 3.3 |

The expression amount of BST1 gene was significantly correlated to the prognosis of colorectal cancer patients (P=0.02). The high expression of this gene will increase the risk of death of colorectal cancer patients. The risk ratio was 3.3, indicating that the increase of each unit in the expression amount of this gene will increase the risk of death of patients by 3.3 times.

(2) MGST1 (Microsomal Glutathione S-Transferase 1)

| Gene symbol | Wald statistic | P value | risk ratio |
|---|---|---|---|
| MGST1 | 6.4 | 0.01 | 4.5 |

The expression amount of MGST1 gene was significantly correlated to the prognosis of colorectal cancer patients (P=0.01). The high expression of this gene will increase the risk of death of colorectal cancer patients. The risk ratio was 4.5, indicating that the increase of each unit in the expression amount of this gene will increase the risk of death of patients by 4.5 times.

(3) HP (Haptoglobin)

| Gene symbol | Wald statistic | P value | risk ratio |
|---|---|---|---|
| HP | 7.7 | 0.005 | 2.3 |

The expression amount of HP gene was significantly correlated to the prognosis of colorectal cancer patients (P=0.005). The high expression of this gene will increase the risk of death of colorectal cancer patients. The risk ratio was 2.3, indicating that the increase of each unit in the expression amount of this gene will increase the risk of death of patients by 2.3 times.

(4) RCAN3 (RCAN Family Member 3)

| Gene symbol | Wald statistic | P value | risk ratio |
|---|---|---|---|
| RCAN3 | 11.8 | 0.001 | 0.6 |

The expression amount of RCAN3 gene was significantly correlated to the prognosis of colorectal cancer patients (P=0.001). The low expression of this gene will increase the risk of death of colorectal cancer patients. The risk ratio was 0.6, indicating that the decrease of each unit in the expression amount of this gene will increase the risk of death of patients by 1.7 times.

(5) SRA1 (Steroid Receptor RNA Activator 1)

| Gene symbol | Wald statistic | P value | risk ratio |
|---|---|---|---|
| SRA1 | 17.7 | 0.001 | 0.1 |

The expression amount of SRA1 gene was significantly correlated to the prognosis of colorectal cancer patients (P=0.001). The low expression of this gene will increase the risk of death of colorectal cancer patients. The risk ratio was 0.1, indicating that the decrease of each unit in the expression amount of this gene will increase the risk of death of patients by 10 times.

2. The Correlation Between the Expression Amounts of Five Genes and the Prognosis of Colorectal Cancer The inventors used prevailing R statistic language, "e1071" software package, invoked support vector machine algorithm, and combined the expression data of the 5 genes in the above 54 samples, to establish a categorizing model. Based on this categorizing model, the prognosis index of each colorectal cancer patient to be tested could be calculated.

If the prognosis index of a sample is larger than 0, it will be categorized as a high risk case; and if the prognosis index of a sample is lower than 0, it will be categorized as a low risk case. 25 patients of group 1 in Example 1 were categorized into the high risk group, and 29 patients were categorized into the low risk group. 20 cases of the 25 patients in the high risk group were dead, while only 3 cases of the 29 patients in the low risk group were dead, indicating that the prognosis of the low risk group was significantly better than the high risk group. The P value of Log-rank test is less than 0.001, with statistical significance. Kaplan-Meier curve and Log-rank test were adopted to compare the survival rates of the patients in the two groups. Kaplan-Meier curves can be seen in FIG. 1. Multiple factor COX regression analysis was adopted to compare the pathologic TNM staging and the prediction model of the 5 genes in respect to the performances for evaluating the prognosis of patients, and the results are shown in Table 1. The prediction results of both the TNM staging and the 5 genes were significantly correlated to the prognosis of patients (P value less than 0.01), and the prediction model of the 5 genes can provide information, which is independent of current clinical pathologic staging, and which can be used for evaluating the risk of death of patients.

TABLE 1

| Prognosis factor | B | Exp(B) | Wald | Sig. |
|---|---|---|---|---|
| TNM staging | 1.06 | 2.88 | 12.38 | 0.001 |
| 5-gene Signature | 1.75 | 5.75 | 7.34 | 0.007 |

Figure 2:
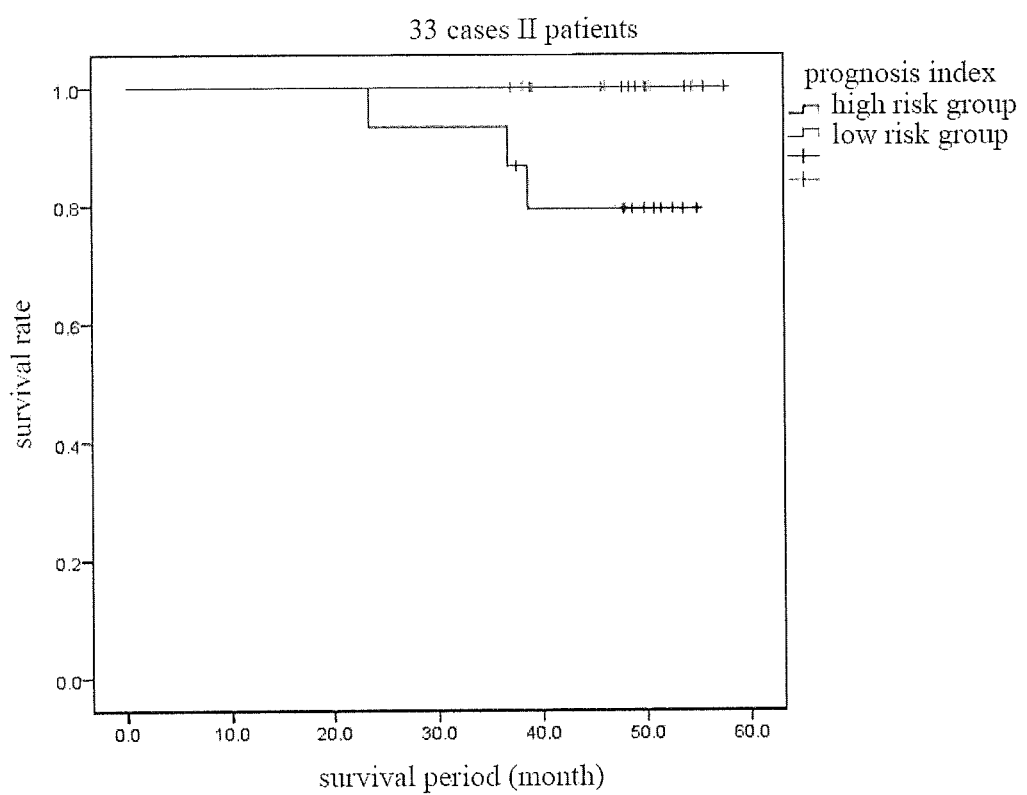
FIG. 2: Kaplan-Meier curve of the 33 cases of stage II patients in group 2.

According to the method of Example 3, the expression levels of the 5 genes were detected in the blood samples of the 33 stage II patients in group 2 of Example 1. Based on the expression levels of the 5 genes, the above mentioned categorizing model was used to calculate the prognosis indexes. 15 patients were categorized into the high risk group, and 18 patients were categorized into the low risk group. Kaplan-Meier curve and Log-rank test were adopted to compare the survival rates of the patients in the two groups. The Kaplan-Meier curve is shown in FIG. 2.

Figure 3:
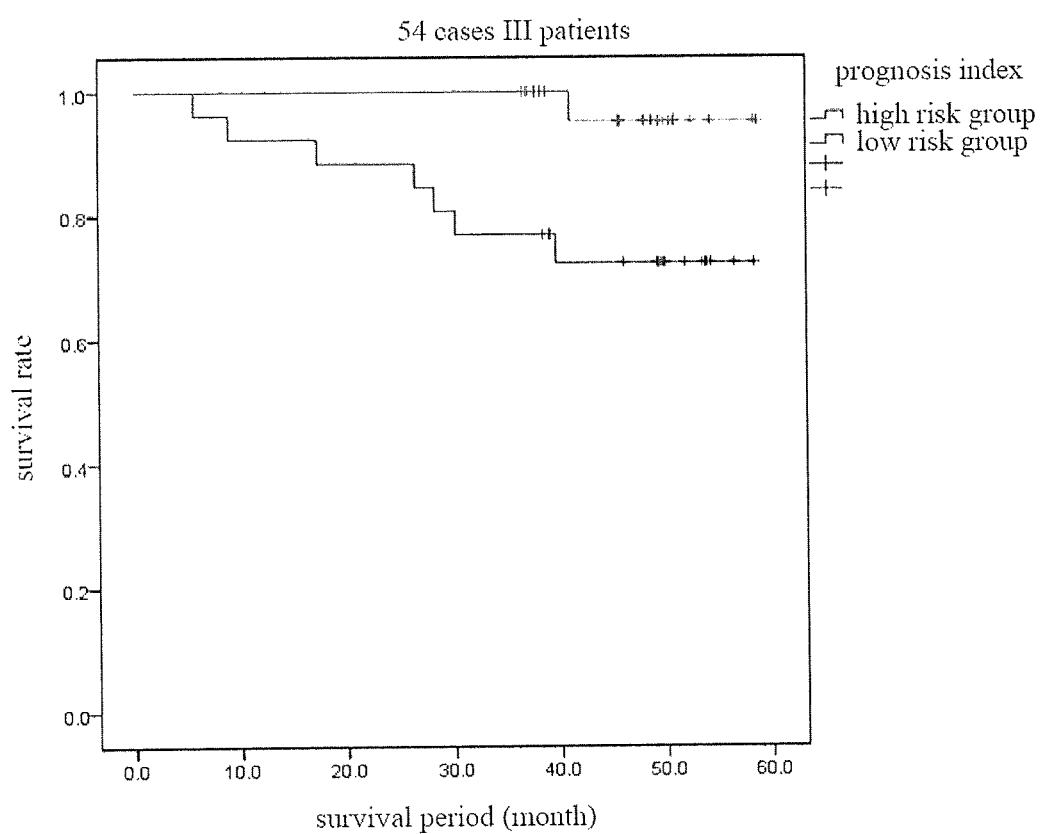
FIG. 3: Kaplan-Meier curve of the 54 cases of stage III patients in group 2.

According to the method of Example 3, the expression levels of the 5 genes were detected in the blood samples of the 54 stage III patients in group 2 of Example 1. Based on the expression levels of the 5 genes, the above mentioned categorizing model was used to categorize and calculate the prognosis indexes. 26 patients were categorized into the high risk group, and 28 patients were categorized into the low risk group. Kaplan-Meier curve and Log-rank test were adopted to compare the survival rates of the patients in the two groups. The Kaplan-Meier curve is shown in FIG. 3.

Meantime, disease developments of the above samples were observed, and 3 cases of the 15 patients in stage II high risk group were dead, while the 18 patients in low risk group all survived, indicating that the prognosis of the low risk group was better than that of the high risk group. The P value of Log-rank test is equal to 0.05, with statistical significance; 7 cases of the 26 patients in stage III high risk group were dead, while 1 case of the 28 patients in low risk group was dead, indicating that the prognosis of the low risk group was better than that of the high risk group. The P value of Log-rank test is equal to 0.016, with statistical significance.

The above results were summarized, as shown in Table 2:

TABLE 2

|  | Stage II | | Stage III | |
|---|---|---|---|---|
| Detection Results | High risk 15 cases | Low risk 18 cases | High risk 26 cases | Low risk 28 cases |
| Actual development | 3 died, 12 survived | All survived | 7 died, 19 survived | All survived |

It can be seen from the above results that the kit of the invention can achieve accurate prognosis for colorectal cancer, because all of the died patients suffering from colorectal cancer come from the high risk population predicted by the kit of the invention, while all of the survived patients suffering from colorectal cancer come from the low risk population predicted by the kit of the invention.

Example 4

Composition of the Kit of the Invention and Examination of the Samples to be Tested 1. Composition of the Kit
Real-time quantitative PCR detection kit (for 50 persons):
(1) Total RNA Extraction Reagents
PAXgene™ blood RNA system.
(2) Reverse Transcription Reagents
Reverse transcriptase (50 ul); reverse transcription buffer (200 ul); genome DNA removing buffer (100 ul); primers (50 ul); enzyme free water (1.9 ml); PCR reaction plate: 384-well plate containing forward primer solution and reverse primer solution.
Primer pairs for housekeeping genes:

```
1. CSNK1G2

F:5'-GCCGCAGTGATGATGTTCTAGC-3' (SEQ ID NO: 35)

R:3'-TCTGCTGCCGTGCAAATC-5' (SEQ ID NO: 36)
```

```
2. DECR1:

F:5'-CGATGCTACCACCTAATAGT-3' (SEQ ID NO: 37)

R:3'-TAGGCTGGACAGAAGAGT-5' (SEQ ID NO: 38)
```

```
3. FARP1:

F:5'-ACCTGTCGTTATTCCTATATCC-3' (SEQ ID NO: 39)

R:3'-GAAACCGTGTTCCCTGTG-5' (SEQ ID NO: 40)
```

Primer pairs for the target genes:

```
1. BST1:

F:5'-ATAGCCACCTCCTTGTTA-3' (SEQ ID NO: 25)

R:3'-TAATCGAGTCCAGAGTCAT-5' (SEQ ID NO: 26)
```

```
2. MGST1:

F:5'-TAGAACGTGTACGCAGAG-3' (SEQ ID NO: 27)

3'-CAATGGTGTGGTAGATCC-5' (SEQ ID NO: 28)
```

```
3. HP:

F:5'-GGTTCAGAAGACCATAGC-3' (SEQ ID NO: 29)

R:3'-ATCTTATCGCATCCACTC-5' (SEQ ID NO: 30)
```

```
4. RCAN3:

F:5'-ACCAGGAAGGAACAGAAC-3' (SEQ ID NO: 31)

R:3'-AGAACGAAACCACAATGAC-5' (SEQ ID NO: 32)
```

```
5. SRA1:

F:5'-GCAGCCAATGAAGAGAAA-3' (SEQ ID NO: 33)

R:3'-GGGAACCGAGGATTATGA-5' (SEQ ID NO: 34)
```

(3) cDNA Amplification Reagents
Mixed buffer containing a reactive enzyme and a fluorescent dye (20 ml); ROX reference dye (800 ul) PCR reaction plate: PCR reaction plate: same as the PCR reaction plate in the reverse transcription reagents.

2. Using Method of the Kit
(1) 2.5 ml peripheral blood of the participants to be tested was collected into PAXgene™ blood RNA tube (PreAnalytix GmbH, Hombrechtikon, CH), and was treated in accordance to the manufacture's instructions; according to the instructions provided by the manufacture, and PAXgene™ blood RNA system (PreAnalytix) was used to extract samples to be tested.

(2) Reverse Transcription
Using the total RNA of step (1) as a template and the above reverse transcription reagents, the cDNAs of 5 target genes and housekeeping genes were obtained.

(3) cDNA Amplification
Using the cDNAs obtained in step (2) as a template and the above cDNA amplification reagents for amplification, Biosystems 7900HT Fast Real-Time PCR system was used to detect the amount of the cDNAs.

(4) The detected expression levels of the 5 genes were input into support vector machine model, to calculate prognosis indexes. If the prognosis index of a sample is larger than 0, it will be categorized as a high risk case; and if the prognosis index of a sample is lower than 0, it will be categorized as a low risk case.

Note: in the kit of the invention, with respect to the number of the primer pairs for target genes, any one or more primer pairs can be selected according to actual requirements.

In summary, the 5 genes of the invention are closely related to the development of colorectal cancer, and the high/low expression(s) of these genes will significantly increase the fatalness of colorectal cancer. The development situation of colorectal cancer in patients can be determined by separately or simultaneously detecting the expression level(s) of the 5 genes, with high accuracy.

The invention claimed is:

1. A method for detecting gene expression, comprising:
   obtaining a blood sample collected from a human having colorectal cancer; and
   detecting expression levels of the BST1, MGST1, HP, RCAN3, and SRA1 genes from the blood sample by hybridization, amplification, or sequencing wherein detecting the expression levels comprises detecting RNA transcripts transcribed from the genes, cDNAs complementary to the RNA transcripts, or cRNAs complementary to the cDNAs, wherein:
   the BST1 gene has the nucleotide sequence shown in SEQ ID NO: 1;
   the MGST1 gene has the nucleotide sequence shown in SEQ ID NO: 2, 3, 4, 5, 6, 7, 8, 9, or 10;
   the HP gene has the nucleotide sequence shown in SEQ ID NO: 11 or 12;
   the RCAN3 gene has the nucleotide sequence shown in SEQ ID NO: 13, 14, 15, 16, 17, 18, 19, 20, 21, or 22; and
   the SRA1 gene has the nucleotide sequence shown in SEQ ID NO: 23 or 24.

2. The method according to claim 1, wherein detecting the expression levels comprises detecting the RNA transcripts.

3. The method according to claim 1, wherein detecting the expression levels comprises detecting the cDNAs.

4. The method according to claim 1, wherein detecting the expression levels comprises detecting the cRNAs.

5. The method according to claim 1, wherein detecting the expression levels comprises performing a reverse-transcription polymerase chain reaction.

6. The method according to claim 1, wherein detecting the expression levels comprises using oligonucleotides.

7. The method according to claim 1, wherein detecting the expression levels comprises using primers.

8. The method according to claim 1, wherein detecting the expression levels comprises using hybridization probes.

9. The method according to claim 1, wherein detecting the expression levels comprises using hybridization probes and primers.

10. The method according to claim 1, wherein detecting the expression levels comprises using oligonucleotides that hybridize with the RNA transcripts.

11. The method according to claim 1, wherein detecting the expression levels comprises using oligonucleotides that hybridize with the cDNAs.

12. The method according to claim 1, wherein detecting the expression levels comprises:
   amplifying the RNA transcripts to obtain amplified products; and
   detecting the amounts of the amplified products using primers.

13. The method according to claim 1, wherein detecting the expression levels comprises:
   amplifying the RNA transcripts to obtain the cDNAs;
   hybridizing probes to the cDNAs to obtain hybridization products; and
   detecting the amounts of the hybridization products.

14. The method according to claim 1, wherein detecting the expression levels comprises using oligonucleotides comprising the nucleotide sequences shown in SEQ ID NOs: 25-34.

15. A method for prognosis of colorectal cancer, comprising:
   obtaining a blood sample collected from a patient having colorectal cancer;
   detecting expression levels of the BST1, MGST1, HP, RCAN3, and SRA1 genes from the blood sample by hybridization, amplification, or sequencing wherein detecting the expression levels comprises detecting RNA transcripts transcribed from the genes, cDNAs complementary to the RNA transcripts, or cRNAs complementary to the cDNAs;
   inputting the expression levels of the genes into a support vector machine model to calculate a prognosis index; and
   determining the prognosis of the patient based on the prognosis index, wherein:
   the BST1 gene has the nucleotide sequence shown in SEQ ID NO: 1;
   the MGST1 gene has the nucleotide sequence shown in SEQ ID NO: 2, 3, 4, 5, 6, 7, 8, 9, or 10;
   the HP gene has the nucleotide sequence shown in SEQ ID NO: 11 or 12;
   the RCAN3 gene has the nucleotide sequence shown in SEQ ID NO: 13, 14, 15, 16, 17, 18, 19, 20, 21, or 22; and
   the SRA1 gene has the nucleotide sequence shown in SEQ ID NO: 23 or 24.

16. The method according to claim 15, wherein detecting the expression levels comprises detecting the RNA transcripts.

17. The method according to claim 15, wherein detecting the expression levels comprises detecting the cDNAs.

18. The method according to claim 15, wherein detecting the expression levels comprises detecting the cRNAs.

19. The method according to claim 15, wherein detecting the expression levels comprises performing a reverse-transcription polymerase chain reaction.

20. The method according to claim 15, wherein detecting the expression levels comprises using oligonucleotides.

21. The method according to claim 15, wherein detecting the expression levels comprises using primers.

22. The method according to claim 15, wherein detecting the expression levels comprises using hybridization probes.

23. The method according to claim 15, wherein detecting the expression levels comprises using hybridization probes and primers.

24. The method according to claim 15, wherein detecting the expression levels comprises using oligonucleotides that hybridize with the RNA transcripts.

25. The method according to claim 15, wherein detecting the expression levels comprises using oligonucleotides that hybridize with the cDNAs.

26. The method according to claim 15, wherein detecting the expression levels comprises:
  amplifying the RNA transcripts to obtain amplified products; and
  detecting the amounts of the amplified products using primers.

27. The method according to claim 15, wherein detecting the expression levels comprises:
  amplifying the RNA transcripts to obtain the cDNAs;
  hybridizing probes to the cDNAs to obtain hybridization products; and
  detecting the amounts of the hybridization products.

28. The method according to claim 15, wherein detecting the expression levels comprises using oligonucleotides comprising the nucleotide sequences shown in SEQ ID NOs: 25-34.

* * * * *